United States Patent
Ran et al.

(10) Patent No.: US 8,927,294 B2
(45) Date of Patent: Jan. 6, 2015

(54) BEAD READER

(75) Inventors: Boaz Ran, Haifa (IL); Chanan Sluszny, Shimshit (IL); Shay Nimri, Kibbutz Nir David-Doar-Na Emek HaMaAyanot (IL)

(73) Assignee: Bio-Rad Laboratories Inc., Hercules, CA (US)

(*) Notice: Subject to any disclaimer, the term of this patent is extended or adjusted under 35 U.S.C. 154(b) by 294 days.

(21) Appl. No.: 12/954,955

(22) Filed: Nov. 29, 2010

(65) Prior Publication Data

US 2011/0136250 A1 Jun. 9, 2011

Related U.S. Application Data

(60) Provisional application No. 61/264,873, filed on Nov. 30, 2009.

(51) Int. Cl.
| | | |
|---|---|---|
| *G01N 21/00* | (2006.01) | |
| *G01N 21/76* | (2006.01) | |
| *G01N 21/64* | (2006.01) | |
| *G01N 21/78* | (2006.01) | |
| *G01N 35/00* | (2006.01) | |
| *G01N 15/06* | (2006.01) | |
| *G01N 15/14* | (2006.01) | |
| *G01N 35/10* | (2006.01) | |

(52) U.S. Cl.
CPC ............ *G01N 21/76* (2013.01); *G01N 21/6428* (2013.01); *G01N 21/6452* (2013.01); *G01N 21/6456* (2013.01); *G01N 21/78* (2013.01); *G01N 35/0098* (2013.01); *G01N 15/0612* (2013.01); *G01N 15/1463* (2013.01); *G01N 2015/1486* (2013.01); *G01N 2021/6419* (2013.01); *G01N 2021/6421* (2013.01); *G01N 2035/1046* (2013.01)
USPC ..... 436/164; 436/172; 422/82.05; 422/82.08; 250/458.1; 250/459.1

(58) Field of Classification Search
None
See application file for complete search history.

(56) References Cited

U.S. PATENT DOCUMENTS

| | | | |
|---|---|---|---|
| 5,981,180 A | | 11/1999 | Chandler et al. |
| 2007/0064990 A1 | | 3/2007 | Roth |

(Continued)

FOREIGN PATENT DOCUMENTS

| | | |
|---|---|---|
| EP | 1729113 | 12/2006 |
| JP | 1-172755 | 7/1989 |
| JP | 2006-337257 | 12/2006 |

OTHER PUBLICATIONS

Wikipedia "ELISA", Wikipedia, the Free Encyclopedia, 6 P., Jan. 30, 2011.

(Continued)

*Primary Examiner* — Robert Xu

(57) ABSTRACT

A method of determining a normalized quantity of an analyte adhering to beads in a detection area of a bead-based assaying system, the method comprising:
  a) causing a complex of the analyte to fluorescently or chemically emit a first light, or to release a dye;
  b) measuring an integrated intensity of the first light emitted from the beads in the detection area, or a concentration of the dye released from the beads in the detection area, or both;
  c) causing light to interact with the beads in the detection area, the interaction not depending on whether or how much analyte is adhering to the beads;
  d) measuring a second light resulting from the interaction with the beads which does not depend on the analyte; and
  e) determining the normalized quantity of analyte from the integrated intensity of the first light or concentration of the dye or both, and from the measured second light.

15 Claims, 10 Drawing Sheets

(56) References Cited

U.S. PATENT DOCUMENTS

2007/0281311 A1  12/2007  Roth et al.
2008/0225272 A1* 9/2008  Nishimura et al. ............. 356/73
2008/0246968 A1  10/2008  Kelso et al.

OTHER PUBLICATIONS

International Search Report and the Written Opinion Dated May 25, 2011 From the International Searching Authority Re. Application No. PCT/IL2010/000993.

Communication Relating to the Results of the Partial International Search Dated Feb. 16, 2011 From the International Searching Authority Re. Application No. PCT/IL2010/000993.

International Preliminary Report on Patentability Dated Jun. 14, 2012 From the International Bureau of WIPO Re. Application No. PCT/IL2010/000993.

Notice of Reason for Rejection Dated May 27, 2014 From the Japanese Patent Office Re. Application No. 2012-541621 and Its Translation Into English.

* cited by examiner

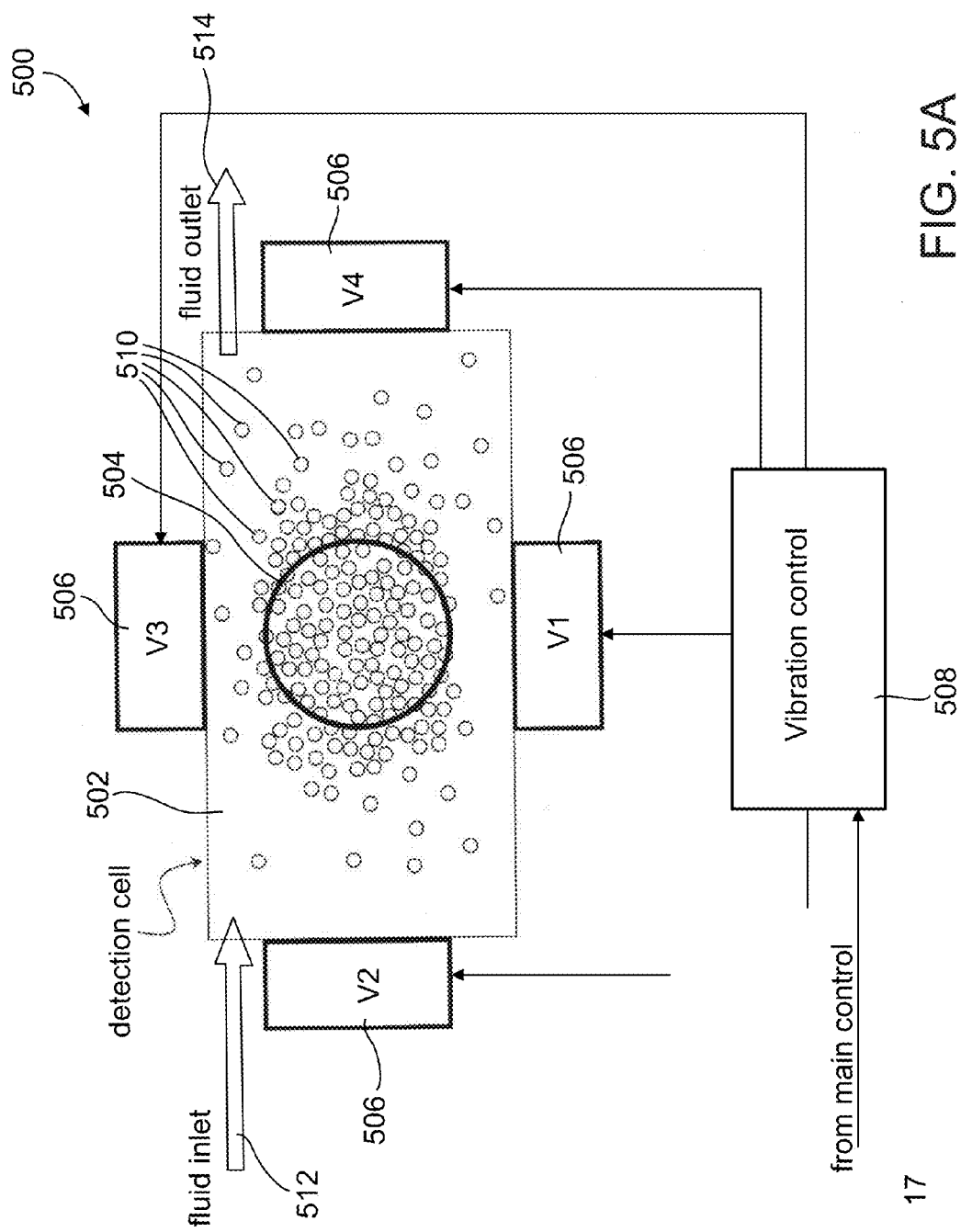

BEAD READER

RELATED APPLICATION

This application claims the benefit of priority under 35 U.S.C. 119(e) from U.S. Provisional Patent Application No. 61/264,873, filed on Nov. 30, 2009, the contents of which are incorporated by reference as if fully set forth herein.

FIELD AND BACKGROUND OF THE INVENTION

The present invention, in some embodiments thereof, relates to a system and method for assaying an analyte in a fluid using beads, and, more particularly, but not exclusively, to a biochemical, biological or biomedical assay where the analyte adheres to the beads and is measured by fluorescence.

US published patent application 2007/0281311, to Roth et al, describes a system for measuring emission from microspheres or beads coupled to fluorescent dyes or tags, where the fluorescent dyes or tags indicate or are approximately proportional to a biological reaction. The beads are magnetic, and are immobilized by a magnet in an imaging volume, while they are being imaged by a CCD, many beads at a time. The system is compared to a prior art system using a flow cytometer, in which fluorescent particles are detected serially, one at a time, which is said to be described in U.S. Pat. No. 5,981,180 to Chandler et al.

US published patent application 2007/0064990 to Roth, describes methods of image processing for analyzing images of fluorescent particles, including methods of analyzing a first image of particles having a uniform concentration of fluorescence material, and a second image of particles having an unknown concentration of a fluorescence material.

SUMMARY OF THE INVENTION

An aspect of some embodiments of the invention concerns a bead-based assay of an analyte, in which the beads are concentrated in a detection area using magnetic fields and vibration, and/or the number of beads in the detection area is measured optically, separately from measuring the concentration of analyte adhering to the beads.

There is thus provided, according to an exemplary embodiment of the invention, a method of determining a normalized quantity of an analyte adhering to beads in a detection area of a bead-based assaying system, the method comprising:
  a) causing a complex of the analyte to fluorescently or chemically emit a first light, or to release a dye;
  b) measuring an integrated intensity of the first light emitted from the beads in the detection area, or a concentration of the dye released from the beads in the detection area, or both;
  c) causing light to interact with the beads in the detection area, the interaction not depending on whether or how much analyte is adhering to the beads;
  d) measuring a second light resulting from the interaction with the beads which does not depend on the analyte; and
  e) determining the normalized quantity of analyte from the integrated intensity of the first light or concentration of the dye or both, and from the measured second light.

Optionally, determining the normalized quantity of analyte comprises:
  a) determining a quantity of analyte adhering to the beads in the detection area, from the integrated intensity of the first light or concentration of the dye or both;
  b) estimating a quantity of beads in the detection area from the measured second light; and
  c) normalizing the quantity of analyte using the estimated quantity of beads.

Optionally, measuring the second light comprises acquiring an image of the detection area, and estimating the quantity of beads comprises counting beads in the image using image processing software.

Optionally, measuring the second light comprises measuring an integrated intensity of the second light from the detection area, and determining the normalized quantity of analyte comprises using the integrated intensity of the second light.

Optionally, estimating the quantity of beads comprises estimating using only an integrated intensity of the second light from the detection area, or using only the integrated intensity of the second light from the detection area and one or more calibration parameters.

Optionally, estimating the quantity of beads comprises estimating a quantity proportional to the integrated intensity of the second light from the detection area.

Optionally, the interaction comprises reflection of the light from the beads.

Additionally or alternatively, the interaction comprises refraction of the light through the beads.

Additionally or alternatively, the interaction comprises exciting fluorescent emission from the beads with the light.

Optionally, the complex is caused to emit the first light at a different range of wavelengths than the second light.

Additionally or alternatively, the complex is caused to emit the first light fluorescently with different time dependence than the second light, by illuminating the beads with excitation light with a spectrum that varies with time.

Optionally, the interaction comprises blocking or absorption of the light by the beads, and reflecting from or passing through areas between the beads, by the light.

Optionally, measuring the integrated intensity of the first light, the second light, or both, comprises measuring the light after it has passed through a filter.

Optionally, the complex is caused to emit the first light, and the beads are located in same places when measuring the first light and the second light.

Optionally, the beads are magnetic, and the method also comprises concentrating the beads in the detection area by vibrating the cell while attracting the beads to the detection area using a magnetic field.

There is further provided, in accordance with an exemplary embodiment of the invention, a system for assaying an analyte adhering to beads, the system comprising:
  a) a detection area where the beads with the analyte adhering to them are held;
  b) a first detector which measures one or more of an integrated intensity of a fluorescent or chemical emission of light from the beads, or a release of a dye from the beads, depending on an amount of analyte adhering to them;
  c) a light source which produces light that interacts with the beads in the detection area, the interaction not depending on whether or how much analyte is adhering to the beads;
  d) a second detector, the same as or different from the first detector, which measures a light received from the beads as a result of the interaction;
  e) a controller which uses the measurements of the first and second detectors to determine a normalized quantity of analyte adhering to the beads.

Optionally, the system also comprises a first filter situated to preferentially admit the first light to the first detector when the first detector is measuring the first light.

Additionally or alternatively, the system also comprises a second filter situated to preferentially admit the second light to the second detector when the second detector is measuring the second light.

There is further provided, in accordance with an exemplary embodiment of the invention, a method of concentrating magnetic beads, used for assaying an analyte, in a detection area of a cell, the method comprising vibrating the cell while attracting the beads to the detection area using a magnetic field.

Optionally, vibrating the cell comprises vibrating with a predominant frequency between 30 and 200 Hz.

Optionally, the predominant frequency is between 60 and 100 Hz.

Additionally or alternatively, vibrating the cell comprises vibrating with a peak to peak amplitude of at least 0.5 mm.

Optionally, the peak to peak amplitude is at least 1 mm.

Optionally, vibrating the cell comprises vibrating so that, for horizontal components, vertical components or both, for at least most of the beads, the mass of the bead times maximum acceleration of the bead would be between 0.3 and 10 times the magnetic force on the bead, if the bead were located at the edge of the detection area.

There is further provided, in accordance with an exemplary embodiment of the invention, a system for assaying an analyte adhering to beads, the system comprising:
a) a detection cell with a resting surface for the beads;
b) a magnet situated to attract the beads towards a detection area of the resting surface, when the beads are located on the resting surface;
c) a vibrator which vibrates the detection cell in a manner that facilitates concentration of the beads in the detection area when the magnet is attracting the beads toward the detection area;
d) a first detector which measures one or more of an integrated intensity of a fluorescent or chemical emission of light from the beads in the detection area, or a concentration of a dye released from the beads in the detection area, depending on an amount of analyte adhering to the beads; and
e) a controller which uses the measurements of the first detector to determine a quantity of analyte adhering to the beads.

Optionally, the system also comprises:
a) a light source which produces light that interacts with the beads in the detection area, the interaction not depending on whether or how much analyte is adhering to the beads; and
b) a second detector, the same as or different from the first detector, which measures a second light received from the beads as a result of the interaction;
wherein the controller uses the measurements of the first and second detectors to determine a normalized quantity of analyte adhering to the beads.

Optionally, the vibrator is capable of vibrating the detection cell so that, for at least some of the beads, the mass of the bead, times the maximum acceleration of the detection cell, is greater than the static frictional force between the bead and the resting surface when the magnet is attracting the bead, at least for some part of the resting surface outside the detection area.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 5A is a schematic top view of a detection cell with vibrators and magnets, according to an exemplary embodiment of the invention.

DESCRIPTION OF EMBODIMENTS OF THE INVENTION

Figure 1:
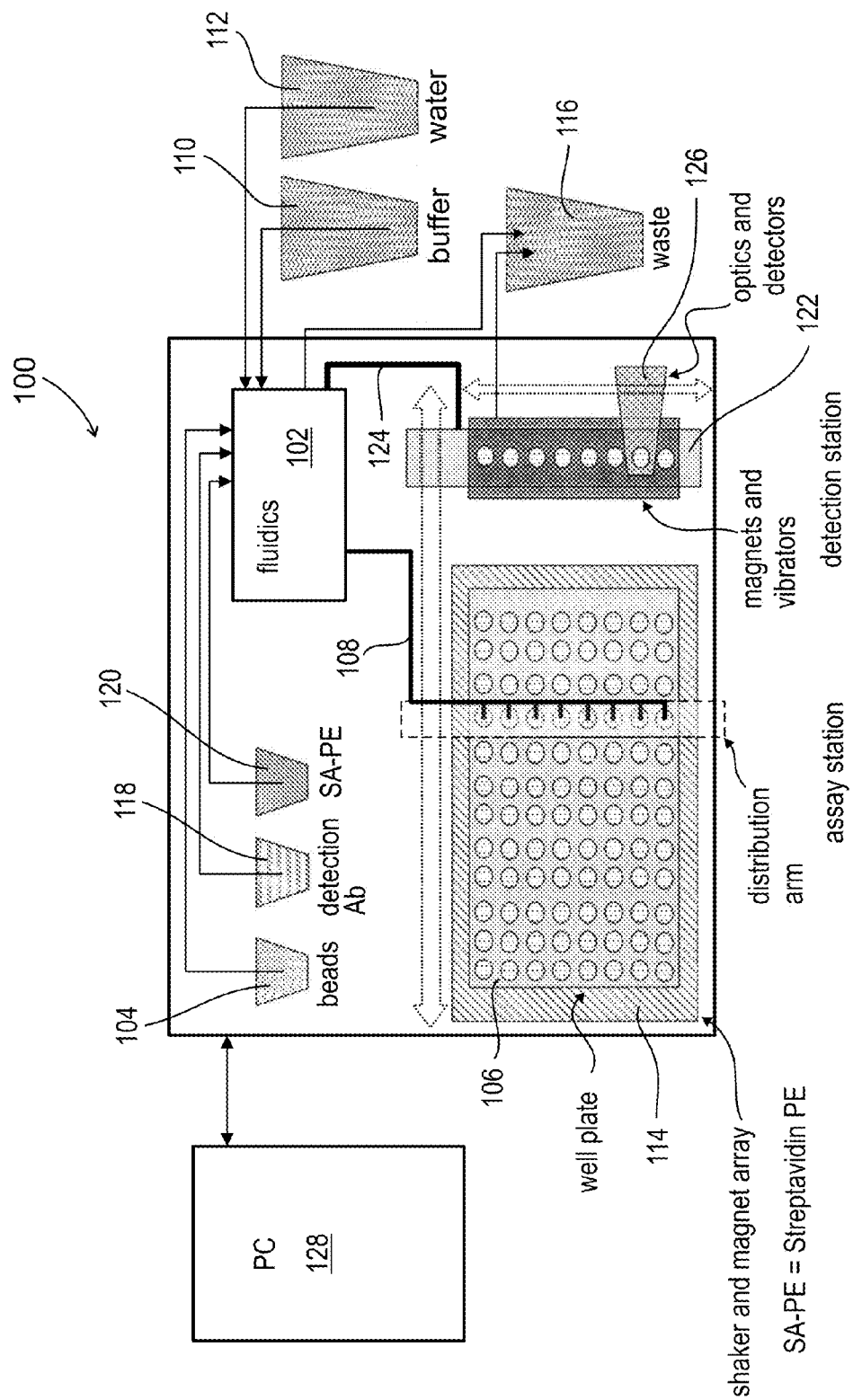
FIG. 1 is a schematic top view of a system for assaying an analyte, according to an exemplary embodiment of the invention.

The present invention, in some embodiments thereof, relates to a system and method for assaying an analyte in a fluid using beads, and, more particularly, but not exclusively, to a biochemical or biological assay where the analyte adheres to the beads and is measured by an assay using fluorescence or chemiluminescence, or by an enzyme-linked assay. Such an assay can be used in biomedical research, as well as for clinical use.

The assay may show the presence or concentration of a known analyte in the fluid sample, for example a biological marker in a blood sample, based on a known tendency of the analyte to bind to a particular ligand. Additionally or alternatively, the assay may show the presence or concentration of any analyte, even a previously unknown analyte, that binds to a particular ligand, for example in order to discover the target of an antibody.

In some embodiments of the invention, the results of the assay do not directly provide a diagnosis of a disease or other abnormal medical condition. In some of those embodiments of the invention, the results of the assay may be used as evidence in making a diagnosis, for example as one of a plurality of factors used in making the diagnosis. In other cases, for example where the assay is used purely for biological research, the results of the assay are not used even indirectly for making a diagnosis. In other embodiments of the invention, the assay is a diagnostic assay, which directly provides a diagnostic result, for example finding the presence or concentration of a marker for a disease.

An aspect of some embodiments of the invention concerns a system and method for performing an assay of an analyte in a fluid, using beads to which the analyte adheres, in which the quantity of analyte adhering to the beads is measured by exciting fluorescent or chemiluminescent emission from a complex of the analyte and measuring the integrated intensity of the emission from all the beads in a detection area, and a separate optical measurement is made of the number of beads present, in order to normalize the quantity of analyte.

Alternatively or additionally, the quantity of analyte adhering to the beads is measured by catalyzing a complex of the analyte to release a dye or a chemiluminescent material into a liquid surrounding the beads, for example using an appropriate enzyme, and optically measuring a concentration of the dye or chemiluminescent material in the liquid. For example, the SuperSignal Chemiluminescent Substrate sold by Pierce uses HRP enzyme to catalyze the excitation of a chemiluminescent material when an analyte binds to a ligand attached to a bead. However, using fluorescent emission to measure the quantity of analyte adhering to the beads has the potential advantage, over chemiluminescent or enzyme-linked assay methods, that the timing of the fluorescent emission can be controlled more precisely. Although the description herein generally refers to using fluorescent emission to measure the quantity of analyte adhering to the beads, it should be understood that such chemiluminescent or enzyme-linked assay methods may also be used to measure the quantity of analyte, and except as noted, other aspects of the description generally apply to those cases as well.

As used herein, expressions such as "fluorescent emission from a complex of the analyte," or "from the analyte complex" and "exciting the analyte complex to fluorescently emit," include both fluorescent emission from the analyte molecule itself, and the more usual case of fluorescent emission from a fluorescent tag molecule attached directly or indirectly to the analyte molecule.

Such a system has a potential advantage over prior art systems in which only one bead at a time is measured, since it does not require the complicated fluidics needed to pass only one bead at a time past the detector. It also has a potential advantage over prior art systems in which the fluorescent emission from the analyte complex is imaged using an array detector, and image processing software is used to count the beads, since such array detectors, in order to measure the low emission power of individual beads, generally have to be very expensive cooled array detectors. Instead, the integrated fluorescent emission from the analyte complex in all the beads in the detection area can be measured by a single detector, which can optionally be relatively insensitive and inexpensive. Alternatively, the single detector is a relatively expensive and sensitive detector, which has the potential advantage that it may make more precise measurements of the emission power than an array detector would, because it measures the integrated emission from many beads, and signal to noise ratio is not critical.

The separate optical measurement of the number of beads present, used for normalizing the quantity of analyte, may also be made by a single inexpensive detector measuring integrated light reflected, refracted, emitted, silhouetted by, or otherwise interacting with all the beads in the detection area. As used herein, "interacting with a bead" includes interacting with a molecule directly or indirectly attached to the bead, such as a fluorescent tag not associated with the analyte. Alternatively, the number of beads present may be measured by using an array detector and imaging software for counting the beads, but the array detector need not be an especially sensitive and expensive one, since the light used to measure the number of beads can be brighter than the fluorescent light emitted by the analyte adhering to the beads.

An aspect of some embodiments of the invention concerns a system and method for performing an assay of an analyte in a fluid, using magnetic beads to which the analyte adheres, in which the beads are concentrated in a detection area using a combination of vibrations and a magnetic field. A gradient in the magnetic field attracts the beads to a detection area on the surface on which they are located, while the vibrations overcome static friction between the beads and the surface, allowing them to move in response to the magnetic force.

Concentrating the beads in the detection area, particularly if they are concentrated fairly densely in a single layer, has the potential advantage that the number of beads in the detection area will not vary very much, so the number of beads can be estimated more accurately, than if the beads are not as concentrated. This is particularly true if the beads are packed into a layer at close to their maximum possible single-layer density, with hexagonal packing, over much of the detection area. But even if the beads are not packed at close to their maximum possible density, the percentage variation in the number of randomly distributed beads over the detection area may be lower, for example in proportion to the square root of the number of beads, if there are more beads present. Having a greater number of beads in the detection area also improves the signal to noise ratio for measuring the quantity of analyte adhering to the beads, which is generally done by exciting fluorescent emission from the analyte complex and measuring its intensity. The power emitted per bead is generally rather low, so it is advantageous to have the beads packed densely in the detection area. This is especially true if the integrated fluorescent emission over the detection area is measured, for example by a single detector.

Optionally, once the beads are concentrated in the detection area, the integrated fluorescent emission from the analyte complex, over the detection area, is measured, and a separate optical measurement is made of the number of beads, in order to normalize the quantity of analyte measured by the fluorescent emission, as described above.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Overall System Configuration and Method

Figure 2:
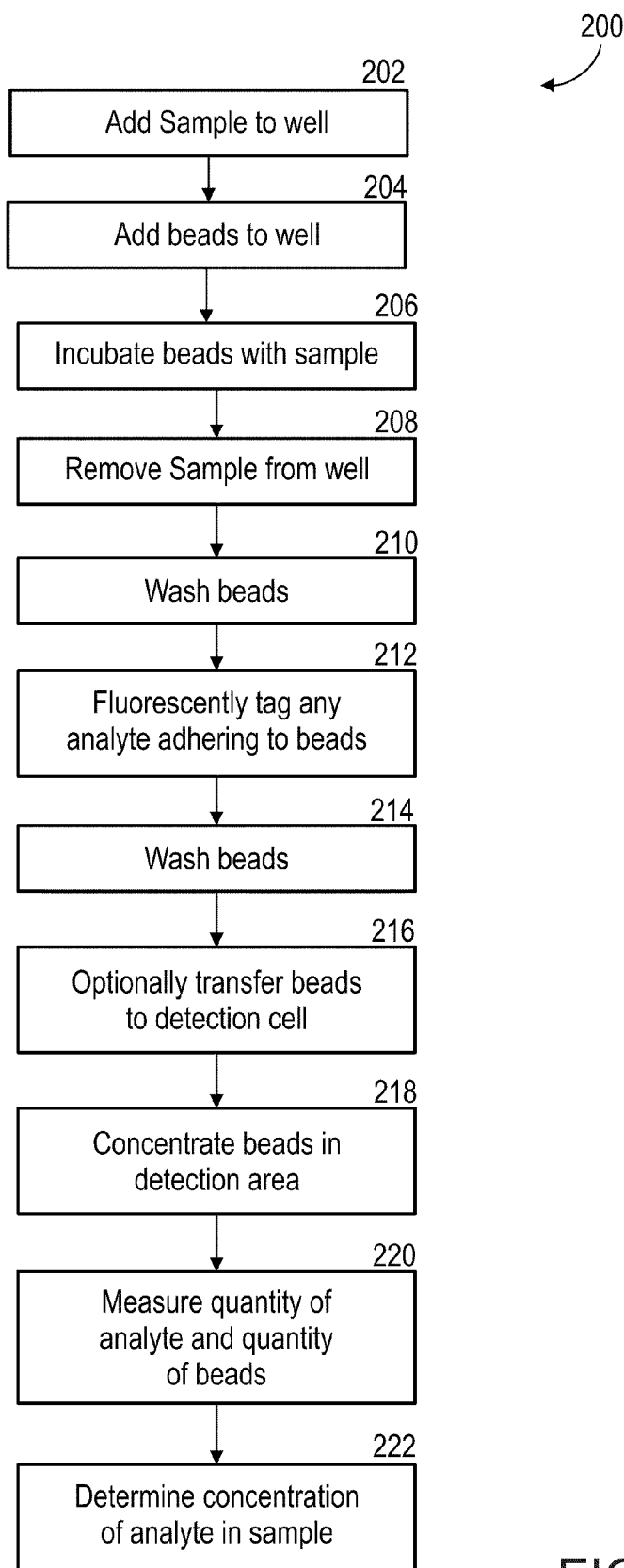
FIG. 2 is a flowchart of a method of assaying an analyte, which is performed using the system of FIG. 1.

Referring now to the drawings, FIG. 1 illustrates a system 100 for assaying an analyte in a sample of fluid, for example for assaying a bio-molecule in a sample of blood or serum. A method of using system 100 will be described with reference to a flowchart 200 in FIG. 2. System 100 is designed to assay a large number of samples automatically or semi-automatically, but the methods described can also be used manually for one sample at a time.

At 202, samples to be analyzed are added to different wells in a well plate 106. At 204, a fluidics sub-system 102 draws beads, suspended in a fluid in a reservoir 104, and transfers them to the wells in well plate 106 that have samples in them. Alternatively, the beads are placed in the wells before the samples. The fluidics sub-system optionally uses vacuum and fluidics or micro-fluidics components, such as pumps, valves and tubes, to move the suspension of beads, and other fluids, between different reservoirs and the well plate. Optionally a distribution arm 108 simultaneously transfers the beads to multiple wells, for example all of the wells in one row of the well plate, and then optionally the distribution arm moves, and/or the well plate moves, and this action is repeated for another group of wells, for example the next row, until beads have been deposited in all the wells for which a sample is to be assayed. The same procedure may be used for transferring other fluids such as a buffer solution in a reservoir 110, and water in a reservoir 112, to and from the wells, as will be described below.

At 206, the beads are incubated with the sample, so that molecules of the analyte adhere to a ligand on the surface of the beads. For example, the ligand may comprise antibodies, coating the surface of the bead, that recognize and capture molecules of the analyte. Optionally the well plate is vibrated, by one or more vibrators coupled to a well plate base 114, which may mix the beads and the sample more effectively, and shorten the time needed for the analyte to adhere to the beads. Mixing of the beads and the sample may also be facilitate by repeatedly drawing the mixture out of the well and putting it back, by the fluidics sub-system. These means of facilitating mixing may also be used in any of the steps described below, where the beads are incubated with another material.

At 208, the sample and other fluids are optionally removed from the well by fluidics sub-system 102, and optionally the beads are washed, for example with water from reservoir 112 or buffer fluid from reservoir 110, at 210. Optionally, base 114 vibrates the well plate during the washing, to facilitate the washing, and this is also optionally done any of the other times when the beads are washed, as described below. Optionally the beads are magnetic, and magnets attached to base 114 keep the beads in the wells when the sample and other fluids are removed, and when water or buffer fluid is removed after washing the beads. For example, the magnets may be arranged to attract the beads to side walls of each well, while the fluid or water is drained from the bottom of the well, or the magnets may attract the beads to the bottom of each well while the fluid or water is suctioned out the top. Alternatively or additionally, there is a filter in place, which fluid can pass through but beads cannot pass through, on a line through which fluid is removed from the well by suction or by gravity. This filter is located, for example, at the bottom of the well, and the beads remain there when fluid or water is removed from the well, but the line closed, for example by a valve, when fluid or water is not being removed. These procedures are also optionally done any of the other times when the beads are washed. The removed fluid or water is optionally transferred by fluidics sub-system 102 to a waste disposal location 116.

At 212, analyte adhering to the beads, if there is any, is optionally fluorescently tagged. This step may be omitted if the analyte itself is already fluorescent. Optionally, a chemiluminescent tag is used instead of a fluorescent tag, and it should be understood that, in many contexts, when fluorescent emission is mentioned herein, chemiluminescent emission may be used instead. Additionally or alternatively, the analyte may be tagged by a dye molecule, which is used in an enzyme-linked assay, as will be explained below.

Optionally, fluorescent tagging of the analyte involves the following steps. First, detection antibodies, stored in reservoir 118, are added to the wells with the beads by fluidics sub-system 102, optionally together with buffer from reservoir 110. The detection antibodies, which may be similar to the capturing antibodies coated on the surface of the beads, attach to the analyte which is adhering to the beads. The beads and detection antibodies are incubated together. The fluid containing the detection antibodies is then optionally removed, and the beads are optionally washed.

The detection antibodies may differ from the capturing antibodies coating the beads, in that they are modified to attach to molecules of a fluorescent tag. For example, the detection antibodies may be biotinylated. After the detection antibodies have been attached to the molecules of analyte, and the beads have optionally been washed, a fluorescent tag material from a reservoir 120 is added to the well by fluidics sub-system 102. A suitable fluorescent tag material, for example, is streptavidin-PE, which bonds to biotinylated antibodies. Other fluorescent tag materials, and other ways to modify the antibodies, are also possible. The fluorescent tag material is incubated with the beads, the fluid is removed, and the beads are optionally washed at 214.

At 216, the beads are optionally transferred, while suspended in fluid, by fluidics sub-system 102, from well plate 106 to a detection station 122. In some embodiments of the invention, the beads are suspended in small droplets of fluid, which are then manipulated, for example electrostatically, to transfer the beads, instead of using a conventional fluidics system. Additionally or alternatively, this technique of manipulating droplets can be used to move the beads around to position them in a detection area, within detection station 122, or within well plate 106.

At detection station 122, the analyte is detected by fluorescent emission from the fluorescent tag, or optionally from the analyte itself if it is fluorescent. As noted above, both these cases are referred to herein as fluorescent emission from the analyte complex. Optionally, detection station 122 has a plurality of detection cells, and beads from different wells in well plate 106 are transferred to different cells in detection station 122, using a distribution arm 124 to deposit the beads in the detection cells. For example, the beads from one row of wells in well plate 106 are transferred to corresponding cells in detection station 122. Optionally, transfer from a plurality of wells to a plurality of corresponding cells is done simultaneously. Alternatively, the transfer is done serially, and, for example, detection station 122 moves relative to distribution arm 124 when preparing to transfer beads to a different cell.

Detection station 122 includes an optics and detector sub-system 126 which detects fluorescent emission from the analyte complex, in each detection cell. Optionally, there is a single detector set with associated optics, which moves from cell to cell, if the detection station has more than one cell. Alternatively, there is more than one detector set with associated optics, or one detector set for each detection cell, and measurements in different detection cells may be made simultaneously. Using multiple detector sets simultaneously may increase the cost of detectors and optics, and the complexity of controlling them, but may speed up the measurement for a large number of samples.

Optionally, detector station 122 also has associated vibrators and/or magnets, whose function will be described below.

In some embodiments of the invention, the beads are not transferred to a separate detection station, but well plate 106 also functions as a detection station, and each well functions as a detector cell. In these embodiments, there are one or more detector sets with associated optics, which detect fluorescent emission from the wells. For example, there may be an arm with as many detector sets as there are wells in a row, which moves from one row of wells to the next, and which can be used to detect fluorescent emission simultaneously in all of the wells in a row. Alternatively there is only a single detector set which moves from well to well, or a different number of detector sets which can detect fluorescent emission from more than one well simultaneously, or from all of the wells simultaneously.

If well-plate 106 is used as a detection station, then optionally the vibrators and magnets associated with base 114 are also used in the detection process, as will be described below. In this case, the magnets are optionally moved relative to the wells, between the incubation procedures and the detection procedure, since the magnets may be used to attract the beads to the sides of the well when fluid is changed during the incubation and washing procedures described above, while the magnets may be used to attract the beads to a detection area in the center of the well, during the detection procedure as will be described below.

At 218, beads are optionally concentrated in a detection area of each detection cell that has beads in it. At 220, the optics and detector sub-system measures fluorescent emission from the analyte complex adhering to the beads in the detection area of each detection cell, to determine a quantity of analyte. Optionally, the optics and detector sub-system also makes a separate optical measurement of the quantity of beads in each detection area, in order to normalize the quantity of analyte to the number of beads. This normalized quantity of analyte is used in 222 to determine a concentration of analyte in the sample that was being tested, for each detection cell. Methods of concentrating the beads and measuring the quantity of analyte and the number of beads are described in more detail below.

In the case where an assay is used to detect the quantity of analyte adhering to the beads, a catalyst, for example an enzyme, is introduced into the detection cell, which catalyzes the analyte complex to release a dye molecule that it is tagged with, into the fluid surrounding the beads in the detection cell. A concentration of the dye in the detection cell is then measured by one or more optical detectors, for example by passing light of different wavelengths through the fluid, and comparing how much light is absorbed at different wavelengths. In some embodiments of the invention, a chemiluminescent molecule is used instead of or in addition to a dye molecule, and its concentration in the fluid is measured by measuring the emitted light. A review of such enzyme-linked immunoassay (ELISA) methods is given in the Wikipedia article on ELISA, downloaded from <www.wikipedia.org/wiki/ELISA> on Nov. 25, 2010.

A controller 128, such as a personal computer, is optionally used to calculate the concentration of analyte in the sample, from the raw data obtained by the detectors. This calculation may take into account the different sensitivities and/or integration times of the different detectors, for example a detector measuring the number of beads, and a detector measuring the quantity of analyte. Optionally, the calculation made by controller 128 is calibrated by first performing tests using different known concentrations of analyte in the sample, and observing the signals from the detectors in each case. For example, tests are optionally performed for 5 to 8 different concentrations of the analyte, covering a range of 3 to 4 orders of magnitude, and tests at a given concentration are optionally repeated one or more times and averaged, to reduce errors. The test results are optionally fitted to a model, for example a model with 5 parameters, to obtain a calibration curve relating the concentration of analyte in the sample to the quantity of analyte measured on the beads, normalized to the number of beads.

Controller 128, or one or more different controllers, is also optionally used to control one or more of the following: the functions of fluidics sub-system 102, the motion of distribution arms 108 and 124, operation of the vibrators associated with well plate 106 and detector station 122, motion of the magnets if they are moveable, a user interface, and functions of the optics and detector sub-system as described below. The user interface optionally allows the user to develop complex protocols for automated tasks that can be performed while the system is left unattended. It also optionally recommends modes of operation to the user; optionally includes an analysis module that analyzes results; optionally graphically shows the user the placement of samples in the plates; and optionally displays the results of measurements in real time, while the measurements are still taking place, as well when they are completed.

Optics and Detector Configurations

FIGS. 3A through 3D show different configurations of the optics and detector sub-system, used for measuring fluorescent emission from the analyte complex, and for measuring the total number of beads in the detection area of a detection cell. These drawings are not drawn to scale, and angles shown in the drawings may not be accurate, for example minors that reflect a light beam by 90 degrees may appear not to be oriented at 45 degrees with respect to the direction of the light beam, although in the actual device they are oriented at 45 degrees.

Figure 3A:
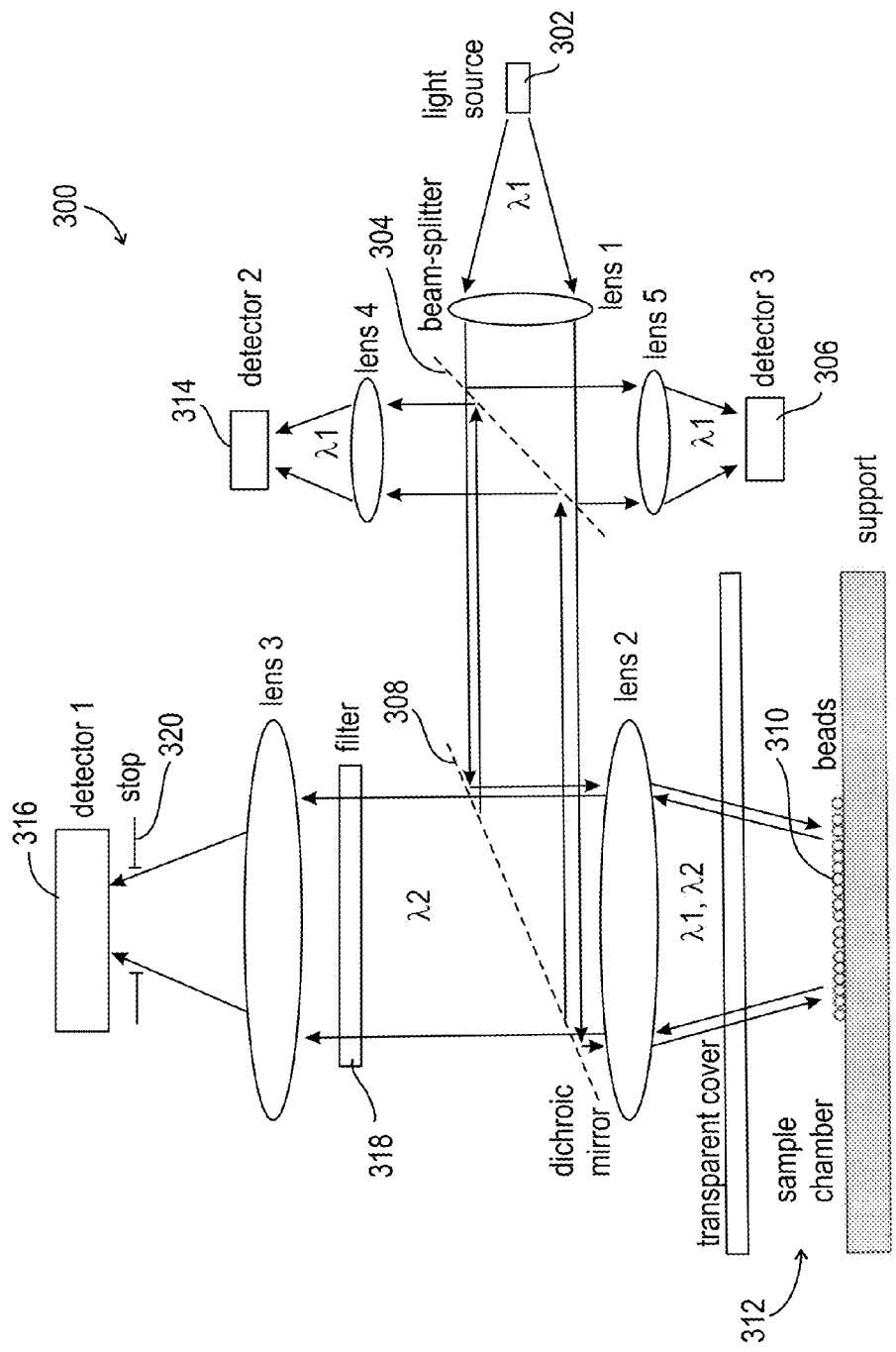
FIGS. 3A-3D are schematic side views of a detection cell and associated illumination and detection optics in a system similar to the system in FIG. 1, each drawing for a different exemplary embodiment of the invention.

FIG. 3A shows an optics and detector configuration 300, with a light source 302 producing a beam of light at a wavelength $\lambda_1$, or a range of wavelengths including $\lambda_1$. For convenience, the light beam, or another light beam, will sometimes be described as behaving in a certain way because of some property of light with wavelength $\lambda_1$, or a different wavelength, but it should be understood in these cases that if the light has a range of wavelengths, these properties also apply to other wavelengths in the range, or to a range of wavelengths including most of the power in the beam. Wavelength $\lambda_1$ is chosen from wavelengths that excite fluorescent emission from the analyte complex. Optionally, light source 302 produces a relatively narrow range of wavelengths, for example less than 100 nm full width half maximum, or less than 50 nm, or less than 20 nm, so that stray light from light source 302 can be easily filtered out of detectors that are intended to detect other wavelengths, for example fluorescent emission from the beads, as will be described below.

The light beam from light source 302 is optionally focused by a lens, and reaches a beam-splitter 304, for example a half-silvered minor. A polarizing beam splitter may also be used, although polarization does not generally play a role in the interaction of the light with the beads. Part of the light beam is optionally reflected by beam-splitter 304 to a detector 306, which is used to monitor the intensity of light source 302. A signal from detector 306 may be used to correct output signals from the other detectors, described below, for variations in the intensity of the light source. Additionally or alternatively, a signal from detector 306 may be used to control the intensity of light source 302, by feedback, keeping it constant. Alternatively, there is no detector 306, and the intensity of light source 302 is optionally monitored and/or controlled by other means, for example internal to light source 302.

The rest of the light beam passes through beam splitter 304, and reaches dichroic minor 308, which reflects light of wavelength $\lambda_1$ towards beads 310, which are shown located at a bottom surface of a detection cell 312. Optionally, the light is focused on the beads by a lens, and passes through a transparent cover of detection cell 312.

The light of wavelength $\lambda_1$ excites fluorescent emission from the analyte complex, with wavelength $\lambda_2$. As explained above for wavelength $\lambda_1$, the phrase "wavelength $\lambda_2$" as used herein may be considered shorthand for "a range of wavelengths including wavelength $\lambda_2$," and statements about properties of light at this wavelength are intended to apply to all wavelengths in the range, or at least to a range of wavelengths that includes the bulk of the power of fluorescent emission. These remarks apply also to the phrase "wavelength $\lambda_3$" used below.

The emitted light of wavelength $\lambda_2$, as well as light of wavelength $\lambda_1$ that is reflected from the beads, pass back through the lens, if there is one, to dichroic mirror 308. Dichroic mirror 308 reflects the light of wavelength $\lambda_1$, which was reflected from the beads, but passes the light of wavelength $\lambda_2$, which was fluorescently emitted from the beads. The passed light of wavelength $\lambda_2$ is measured by a detector 316. Optionally there is a filter 318 in front of detector 316, which removes stray light of other wavelengths that could not have come from the fluorescent emission from the analyte complex. Optionally, there is also a stop 320, which blocks light that did not come from a detection area of detection cell 312, an area on the bottom surface, for example, of detection cell 312, where the beads are optionally concentrated. The stop, the filter, and the lens need not be situated along the path of the emitted light beam in the order shown. The other detectors described, which detect light from the detection area, may also have stops to limit the light they receive to light coming from the detection area, even if not shown in the drawings, and these stops may be situated before, after or between lenses, filters, or other optical elements along the light path. A single stop, situated on a light path before a dichroic minor, may be used to limit the light from two or more different detectors that receive light travelling on that light path, after the light beam is split by a dichroic mirror. Any of the detectors may also use lenses, filters, polarizers, diffusers, and other optical elements, in any order, even if they are not explicitly described, in order to increase the light they receive of a desired range of wavelength and from a desired location, and/or to decrease the light they receive of other wavelengths and from other locations.

Detector 316 responds to an integrated intensity of the emitted fluorescent light from the analyte complex, from the beads in the detection area, rather than producing a useful image of the beads using the relatively low intensity emitted fluorescent light. Optionally, detector 316 is a single detector, which produces a single output signal corresponding to the total intensity of light reaching it, which depends on an integrated intensity of the light emitted from the analyte complex on the beads in the detection area. Alternatively, detector 316 may comprise an array of detector elements, in which the output of each element is added up, using hardware or software, to produce an output signal depending on the integrated intensity of light emitted from the analyte complex on the beads in the detection area. In this case, the individual elements of the array need not be sensitive enough to produce a useful image of the beads using the emitted fluorescent light from the analyte complex.

It should be understood that if chemiluminescence is used instead of or in addition to fluorescence for measuring the quantity of analyte, then the emitted light is not excited by optical excitation of the beads as in the case of fluorescence, and a chemical is added to the detection cell to induce the chemiluminescence of the analyte complex adhering to the beads. If an enzyme-linked assay method is used for measuring the quantity of analyte, then an appropriate enzyme is added to the detection cell, to induce the analyte complex adhering to the beads to emit dye molecules into the fluid surrounding the beads, and a detector, such as detector 316, is used to measure a fraction of light at one or more wavelengths that has been absorbed by the dye molecules, in order to determine a concentration of the dye molecules in the fluid. Optionally in this case, light source 302 is used as the source of light for measuring the concentration of dye molecules, and filters, mirrors, or any other optical elements such as those described above are optionally used to transmit the light of these one or more wavelengths to the detection cell and through the fluid, and then to the detector.

Regardless of the method used, fluorescent, chemiluminescent, enzymatic, or other methods, for determining the concentration of electrolyte, reflected light from the beads is optionally used for estimating the number of beads. In the case of fluorescent emission by the analyte complex, the reflected light from the beads, of wavelength $\lambda_1$, which reflected from dichroic mirror 308, passes back to beam splitter 304, where some of it is reflected to a detector 314, optionally through a lens and a stop. Measurements of the light received by detector 314 are used to estimate the number of beads in the detection area of the detection cell. Optionally, detector 314 produces an output signal which depends on the integrated light reflected from the beads in the detection area. This signal may be used to estimate the number of beads in the detection area, because the amount of light reflected by the beads does not depend on the amount of analyte adhering to them, but only on the number of beads. Alternatively or additionally, detector 314 is an array detector which produces an image of the beads in the detection area. Because the reflected light from the beads may be relatively bright, detector 314 may comprise a relatively inexpensive CCD or CMOS array, such as the array in a digital camera sold for the consumer market. The image produced by detector 314 may then be analyzed by image processing software, to produce a count of the number of beads in the detection area. Using image processing in this way has the potential advantage that the measured number of beads is relatively insensitive to changes in the intensity of light source 302, or to stray light that enters detector 314, as long as there is enough light reflected from the beads, and entering detector 314, to form a clear enough image. Estimating the number of beads from a single signal depending on the integrated light reflected from the beads in the detection area has the potential advantage that it is not necessary to use more than a single detector element, and it is not necessary to run image processing software.

Figure 3B:
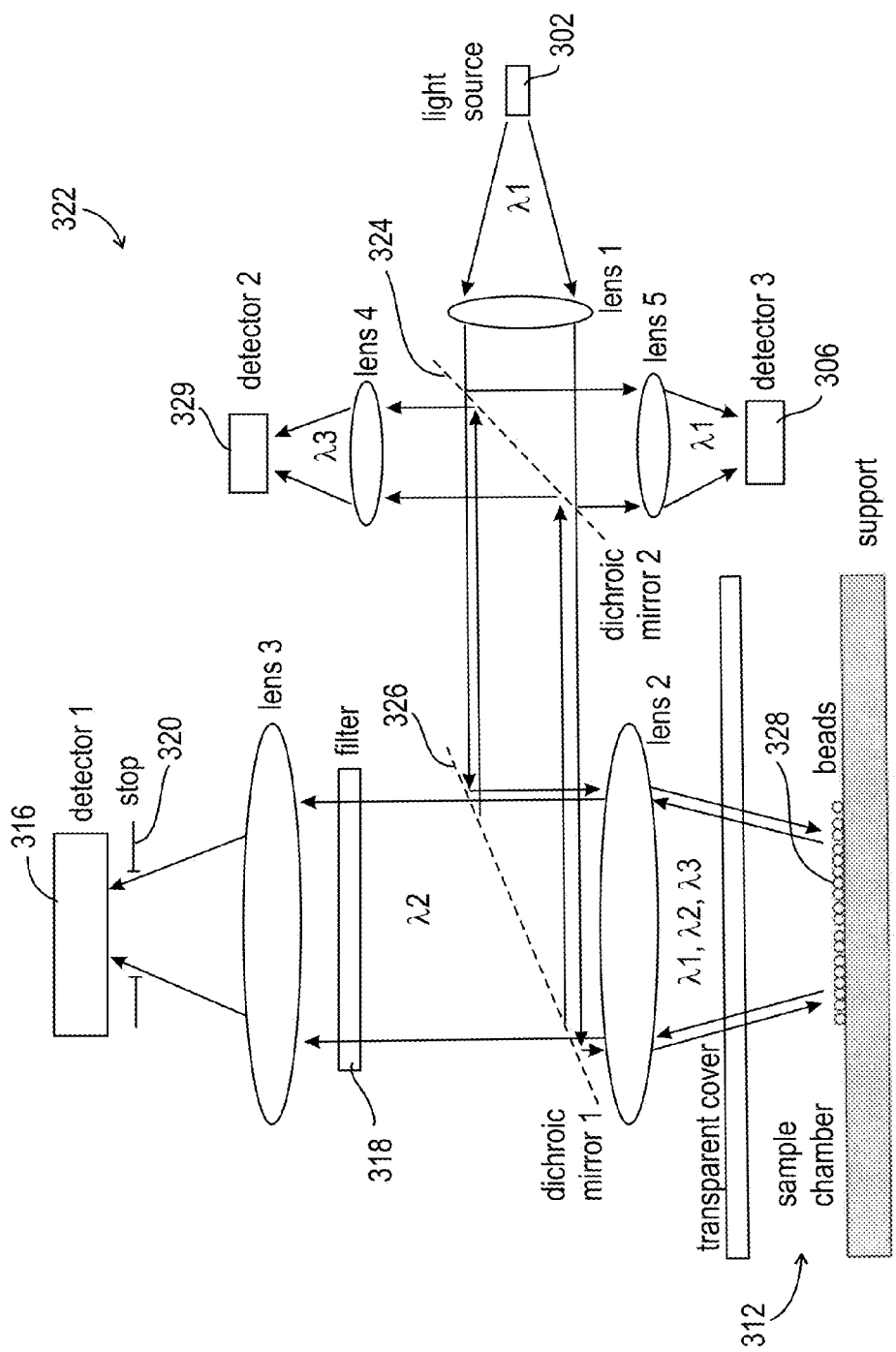

FIG. 3B shows an alternative optics and detector configuration 322. Instead of beam splitter 304, there is a dichroic mirror 324. Much or all of the light of wavelength $\lambda_1$ from light source 302 passes through dichroic mirror 324, but optionally some of the light is reflected to detector 306, which is used to monitor the intensity of light source 302. Alternatively there is no detector 306, in which case little or no light of wavelength $\lambda_1$ need be reflected by dichroic mirror 324, and the intensity of light source 302 may be monitored or regulated by other means, for example by means internal to light source 302. Dichroic minor 326 replaces dichroic minor 308 in FIG. 3A, and like dichroic mirror 308, dichroic minor 326 reflects light of wavelength $\lambda_1$ into detector cell 312, where it illuminates beads 328. Beads 328, in addition to emitting fluorescent light at wavelength $\lambda_2$ from the analyte complex adhering to them, also emit fluorescent light at a wavelength $\lambda_3$, in response to the light of wavelength $\lambda_1$ illuminating them, independent of the analyte adhering to them. The light of wavelength $\lambda_3$, for example, is emitted from a fluorescent dye coated on all the beads by a chemical or biochemical reaction, or embedded in all the beads, not just those with analyte adhering to them.

Emitted light of wavelengths $\lambda_2$ and $\lambda_3$, and any reflected light of wavelength $\lambda_1$, reaches dichroic mirror 326, which passes light of wavelength $\lambda_2$ to detector 316, and reflects light of wavelengths $\lambda_1$ and $\lambda_3$ toward dichroic minor 324. Light of wavelength $\lambda_3$ is reflected from dichroic mirror 324, and reaches detector 329. A signal from detector 329 is used to estimate the number of beads in the detection area of detection cell 312, since the intensity of the emitted light of wavelength of $\lambda_3$ depends on the number of beads, not on the quantity of analyte. A signal from detector 316, as in configuration 300 in FIG. 3A, is used to determine the amount of analyte adhering to the beads. Light of wavelength $\lambda_1$, reaching dichroic minor 324 from dichroic mirror 326, largely or completely passes through dichroic minor 324. Any light of wavelength $\lambda_1$ that does reflect from dichroic minor 324 and reaches detector 329, might not do any harm, since the light of wavelength $\lambda_1$ also has an intensity that is proportional to the number of beads in the detection area. But if desired, light of wavelength $\lambda_1$ may be filtered out by a filter, not shown, located in front of detector 329.

Figure 3C:
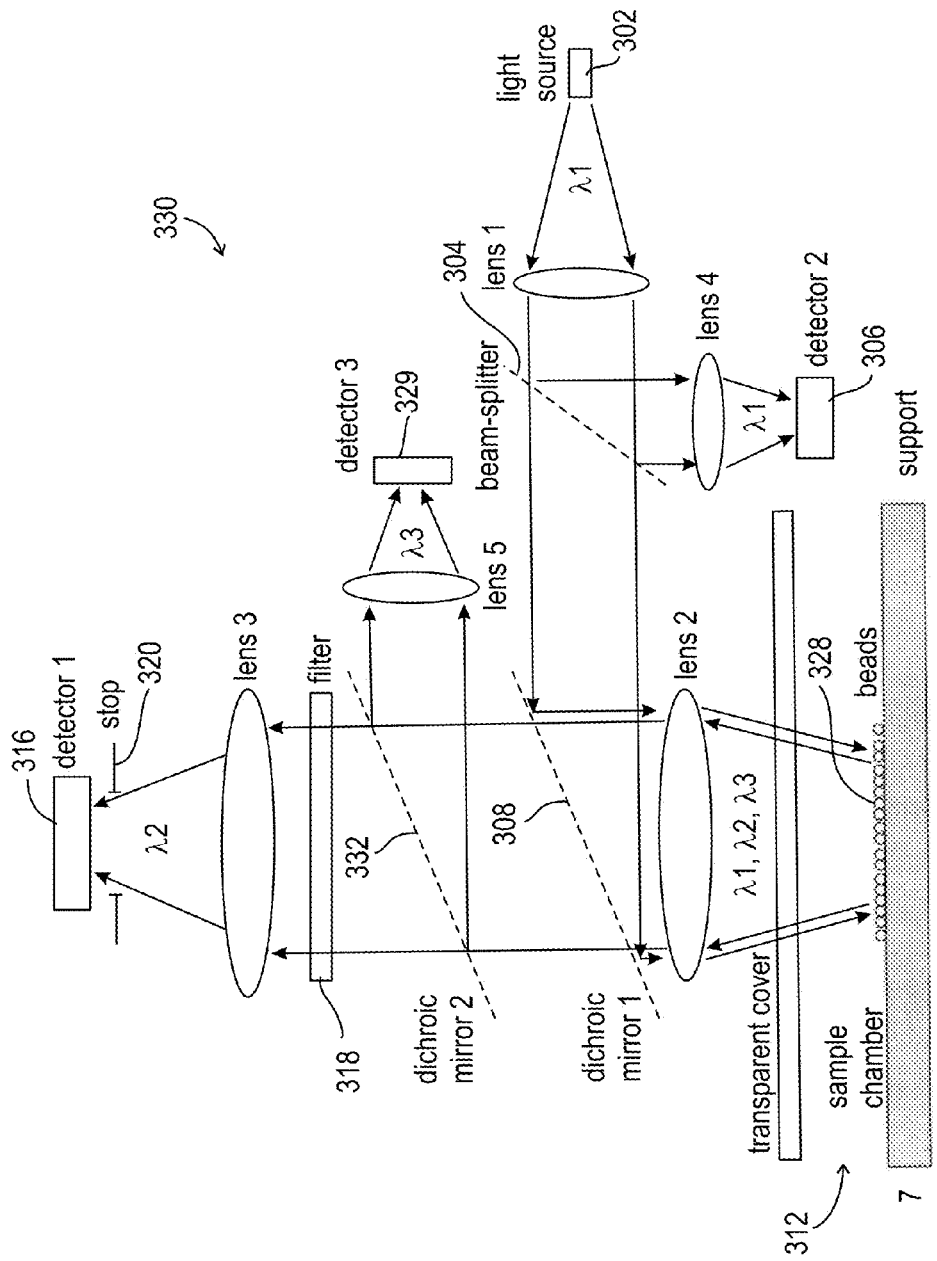

FIG. 3C shows an optics and detector configuration 330, an alternative to the configurations shown in FIGS. 3A and 3B. As in configuration 322 in FIG. 3B, detector cell 312 in configuration 330 has beads 328 which emit fluorescent light at wavelength $\lambda_3$, regardless of how much analyte is adhering to them, in addition to emitting fluorescent light of wavelength $\lambda_2$, from the analyte complex adhering to them. But configuration 330 has a beam-splitter 304 and a dichroic mirror 308 which behave like the corresponding beam-splitter and dichroic minor in configuration 300 in FIG. 3A. In addition, light of wavelength $\lambda_3$, like light of wavelength $\lambda_2$, passes through dichroic mirror 308. A second dichroic mirror 332 then separates light of wavelength $\lambda_2$ from light of wavelength $\lambda_3$, reflecting one, for example wavelength $\lambda_3$, and sending it to detector 329, while transmitting the other, for example wavelength $\lambda_2$, sending it to detector 316. As in configuration 322 in FIG. 3B, a signal from detector 316 is used to estimate the quantity of analyte present in the detection area, and a signal from detector 329 is used to estimate the number of beads present in the detection area.

In a variation of configurations 322 and 330, there are two light sources illuminating the beads, producing different ranges of wavelengths, largely non-overlapping. One of the wavelength ranges excites emission of wavelength $\lambda_2$ from the analyte complex adhering to the beads, while the other wavelength range excites emission of wavelength $\lambda_3$ from a fluorescent material on or in the beads, independent of how much analyte adheres to them. If the two light sources are turned on during different time intervals, with enough time between them so that the fluorescent emission has time to fade, then there is no need to separate light of wavelength $\lambda_2$ from light of wavelength $\lambda_3$ using dichroic minors directing the different wavelengths to different detectors, as in configurations 322 and 330. Instead, both light of wavelength $\lambda_2$ and light of wavelength $\lambda_3$ can be detected by a single detector, for example detector 316, and they can be distinguished by their timing, relative to the timing of the two light sources. Alternatively, dichroic minors and different detectors are used for light of wavelength $\lambda_2$ and light of wavelength $\lambda_3$, and the different timing is used to exclude stray light of the wrong fluorescent wavelength reaching each detector. The on and off timing pattern of the light sources can also be used to distinguish the fluorescent emission from other stray light, which is not correlated with the light from the light sources. This can be done also in configurations such as configurations 300, 322, and 330, where there is only a single light source, by modulating the light source in a known pattern.

Figure 3D:
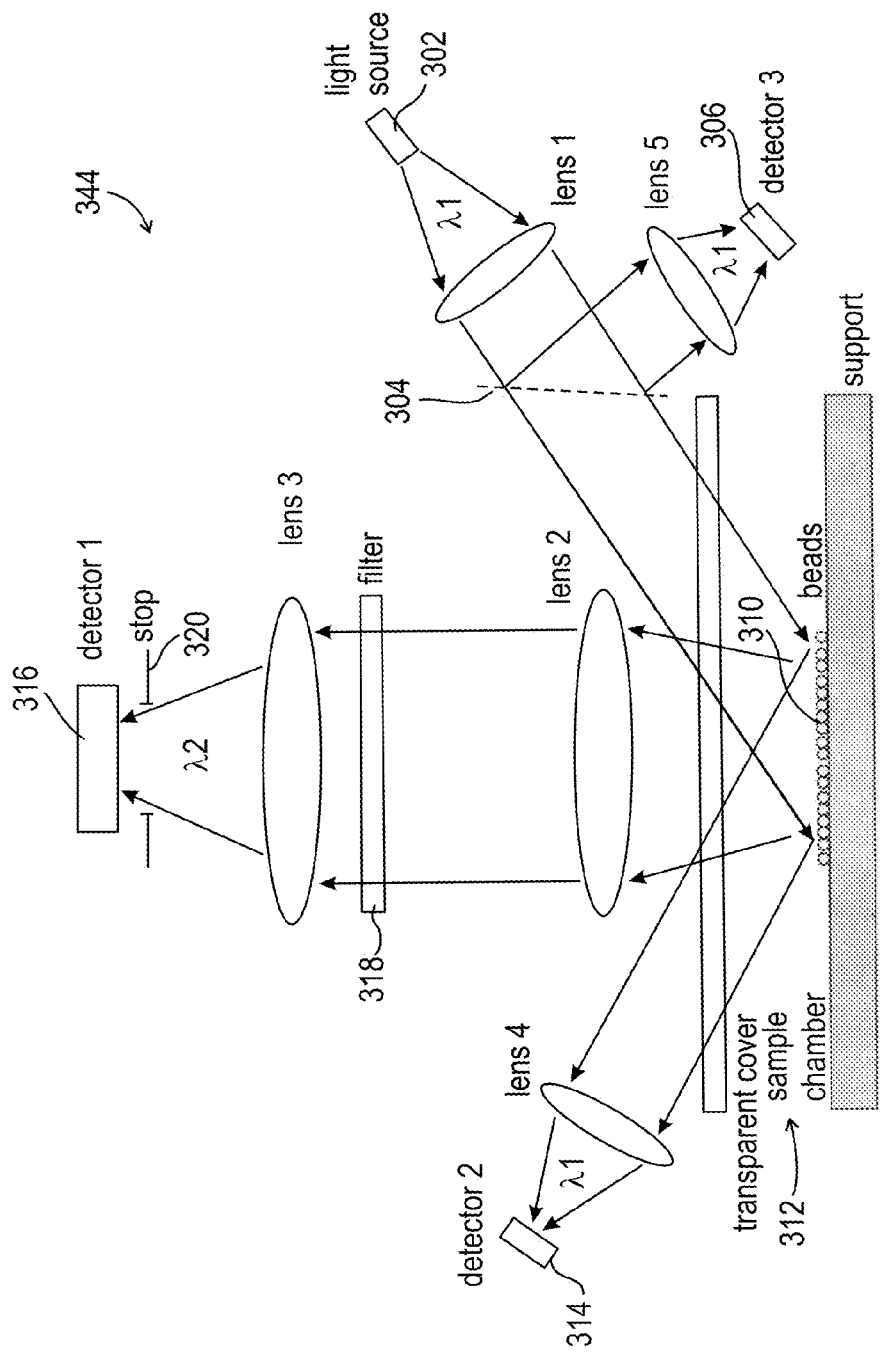

FIG. 3D shows another configuration 334 of optics and detectors, which does not use dichroic mirrors at all. Light source 302 illuminates beads 310 in detection cell 312 directly, with a part of the light from light source 302 optionally monitored by detector 306, as in the other configurations, to monitor its intensity. Detector 314 directly views the beads, to measure an intensity of light reflected from them, and/or to form an image of them to count them. Optionally detector 314 has a filter in front of it, not shown, to block light of wavelength $\lambda_2$ emitted from analyte complex adhering to the beads, although this may not be necessary since the light of wavelength $\lambda_1$ reflected from the beads is likely to be much brighter than light of wavelength $\lambda_2$ emitted from the analyte complex, and if detector 314 forms an image of the beads and they are counted using image processing software, then it will not matter what the intensity of light is. Detector 316 has filter 318 in front of it, which may be an interference filter for example, which passes very little light of wavelength $\lambda_1$, but passes much more of wavelength $\lambda_2$, so that the signal produced by detector 316 is dominated by light of wavelength $\lambda_2$, in spite of the relatively low intensity of light of wavelength $\lambda_2$ emitted from the beads, compared to reflected light of wavelength $\lambda_1$. It may be particularly advantageous in this case to use a narrow range of wavelengths for light source 302, so that a narrow band notch filter can be used to effectively keep light of wavelength $\lambda_1$ out of detector 316, without much reducing the amount of light of wavelength $\lambda_2$ that reaches detector 316. As in configuration 300 in FIG. 3A, a signal from detector 316 is used to estimate the quantity of analyte present in the detection area, and a signal from detector 314 is used to estimate the number of beads present in the detection area.

In a variation on configuration 334, there is only a single detector, for example detector 316, which is used to measure both light of wavelength $\lambda_1$ and light of wavelength $\lambda_2$, by moving filter 318 in and out of the light path in front of detector 316. When filter 318 is in place in front of detector 316, then light of wavelength $\lambda_1$ is largely blocked from entering detector 316, and detector 316 produces an output signal that depends primarily on the intensity of the fluorescent emission of wavelength $\lambda_2$ emitted from the analyte. When filter 318 is moved out of the light path in front of detector 316, then detector 316 will receive mostly light of wavelength $\lambda_1$, which is generally more intense than the light of wavelength $\lambda_2$, and detector 316 will produce an output signal that depends primarily on the intensity of light of wavelength $\lambda_1$ reflected from the beads. Optionally, when filter 318 is moved out of the light path in front of detector 316, another filter, which specifically blocks light of wavelength $\lambda_2$ and admits light of wavelength $\lambda_1$, is moved into the light path in front of detector 316, to further reduce the amount of light of wavelength $\lambda_2$ received by detector 316 at that time.

Moving filter 318, and optionally another filter, in and out of the light path in front of detector 316, may be done mechanically, for example by using a filter wheel which rotates. Alternatively changing filters may be done electronically, for example by using interference filters that are activated or de-activated using the Kerr effect, or by using polarization of liquid crystals, or by similar electronic effects.

Mechanically or electronically switching filters may also be used to switch a single detector from being sensitive to light of wavelength $\lambda_2$ to being sensitive to light of wavelength $\lambda_3$ and back again, instead of using separate detectors for light of wavelength $\lambda_2$ and light of wavelength $\lambda_3$ as described above for configurations 322 and 330.

In other variants of the configurations shown in FIGS. 3A-3D, a multiplexed assay may be performed, in which more than one analyte is assayed simultaneously, by using different fluorescent tags for the different analytes, which emit fluorescence at different wavelengths, and/or which are excited by light of different wavelengths. Different emitted wavelengths may be separated and sent to different detectors by dichroic mirrors. Additionally or alternatively, light emitted by different fluorescent tags may be detected by a same detector and distinguished because they are excited by different excitation light turned on in different time intervals, and/or because the emitted light has different wavelengths, and different filters are switched in and out of the optical path in front of the detector.

Optionally, in a multiplexed assay, ligands for more than one analyte are attached to the same beads, so that the number of beads, used for normalizing the signals from the different analytes, is the same for each analyte. Alternatively, a multiplexed assay is performed using a mixture of different types of beads, which have ligands that bind to different analytes. In this case, the number of beads of each type is optionally measured independently, in order to normalize the signal from each analyte. This may be done, for example, by exciting a fluorescent material on or in the beads, independent of the concentration of the analytes, using a different fluorescent emission wavelength, and/or a different excitation wavelength, for each type of bead. Alternatively, the numbers of some or all of the types of beads are not measured independently, but the different types of beads are homogeneously mixed together, and it is assumed that the ratio of the different types of beads is constant, so that the number of beads of each type may be estimated by measuring the combined number of beads of different types, or the number of beads of one type. However, independently measuring the number of beads of each type has the potential advantage that it avoids statistical errors in the number of beads of each type that would arise from the finite number of beads used, and may allow more accurate results using the same number of beads, or equally accurate results using a smaller number of beads. Reducing the number of beads used can be important, since the cost of the beads may be a major part of the cost of the assay.

In some embodiments of the invention, light from the beads is detected when the beads are covered with water or another liquid, for example in well plate 106, or in detection cell 122. In this case, the beads are optionally viewed through a flat transparent plate which has one side immersed in the liquid, and the other side, facing the detectors, is dry. This configuration has the potential advantage of avoiding distortions in the appearance of the beads, as seen from the detector, due to a curved meniscus or waves on the surface of the liquid.

Figure 4A:
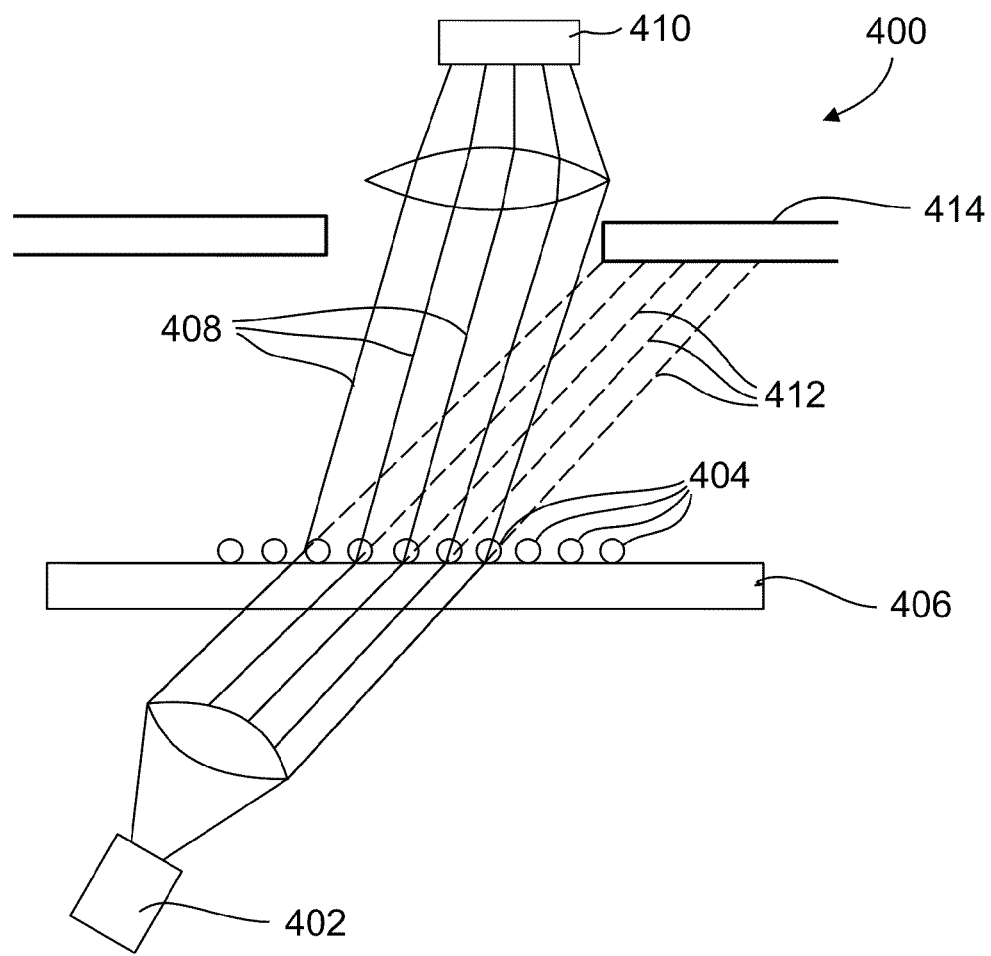
FIG. 4A is a schematic side view of a detection cell and associated illumination optics, according to an exemplary embodiment of the invention.

FIGS. 3A-3D show configurations in which the number of beads is estimated from light reflected from the beads, or fluorescently emitted by the beads. It is also possible to use light refracted from the beads, or silhouetted by the beads, in order to estimate the number of beads. FIG. 4A shows a configuration 400, in which a light source 402 illuminates beads 404 resting on a surface 406 in a detection cell. In this configuration, surface 406 is transparent, and light source 402 is located on the other side of the surface from the beads, i.e. beneath the surface. However, light source 402 could also illuminate the beads from above, for example at an oblique angle as in FIG. 3D, in which case surface 406 need not be transparent. Beads 404 are transparent, and they act like small lenses, refracting light passing through them. Some light rays 408 refracted from beads 404 reach a detector 410. But light source 402 and detector 410 are arranged so that light from light source 402, which is not refracted by the beads, for example light rays 412 which miss the beads, does not reach detector 410, but is blocked by a stop 414 in front of detector 410, for example. The configuration of the light source, the beads, and the detector may also be such that relatively little light reflected from the beads reaches detector 410, because the detector and the light source are almost on opposite sides of the beads. However, in some embodiments of the invention a substantial amount of light reflecting from the beads may also reach detector 410. A signal from detector 410 is used to estimate the number of beads, while another detector, similar to detector 316 is FIGS. 3A-3D, is used to estimate the quantity of analyte adhering to the beads. Optionally, the beads are colored, transmitting only some wavelengths. A filter in front of detector 410 may then preferentially admit those wavelengths, while rejecting much stray light which comes from the light source without passing through the beads. Detector 410 may produce a signal depending on the integrated light from the beads in the detection area, and/or may produce an image which is used to count the beads using image processing software.

Figure 4B:
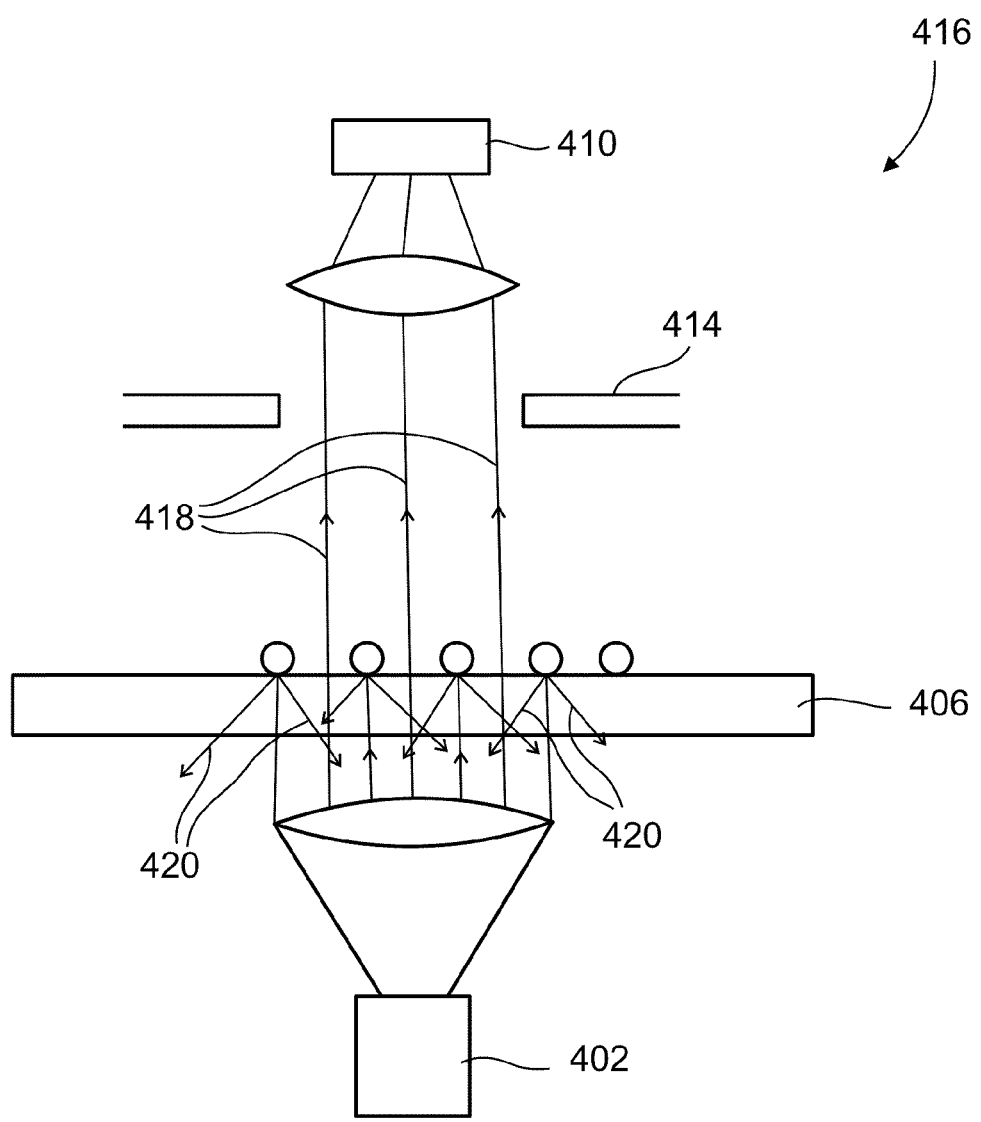
FIG. 4B is a schematic side view of a detection cell and associated illumination optics, according to a different exemplary embodiment of the invention.

FIG. 4B shows a configuration 416, in which a light source 402 illuminates beads 404, from the other side of a transparent surface 406 on which the beads are located. Light source 402 is aimed so that its light reaches detector 410, for light rays, such as light rays 418, which miss beads 404. However, light rays that hit beads 404 are scattered, by reflection from the curved surfaces of the beads, as seen in light rays 420, or by refraction through the curved surfaces of the beads, if the beads are transparent, or by internal scattering if the beads are translucent or opalescent, or by absorption if the beads are dark in color. In all of these cases, the beads block some of the light from reaching detector 410, and a signal from detector 410, measuring the light reaching it, can be used to estimate how many beads are in the detection area. If detector 410 is an imaging detector, the beads will appear dark on a light background, and can be counted by image processing software.

In a variation on configuration 416, light 402 is located on the same side of surface 406 as the beads, i.e. above the surface, and the surface is light in color, or a mirror which reflects the light directly toward detector 410, while the beads are dark. Then the beads will again appear dark on a light background, as seen from detector 410, and a signal from detector 410, either representing an integrated intensity of light reaching the detector from the detection area, or an image of the detection area, can be used to estimate the number of beads in the detection area.

Optionally, controller 128, or one of more other controllers, performs any of the functions of the optics and detector sub-systems described above, including, but not limited to, running image processing software, switching between using different light sources or different detectors, modulating light sources, and switching between different filters.

Concentrating the Beads with Magnets and Vibration

Figure 5B:
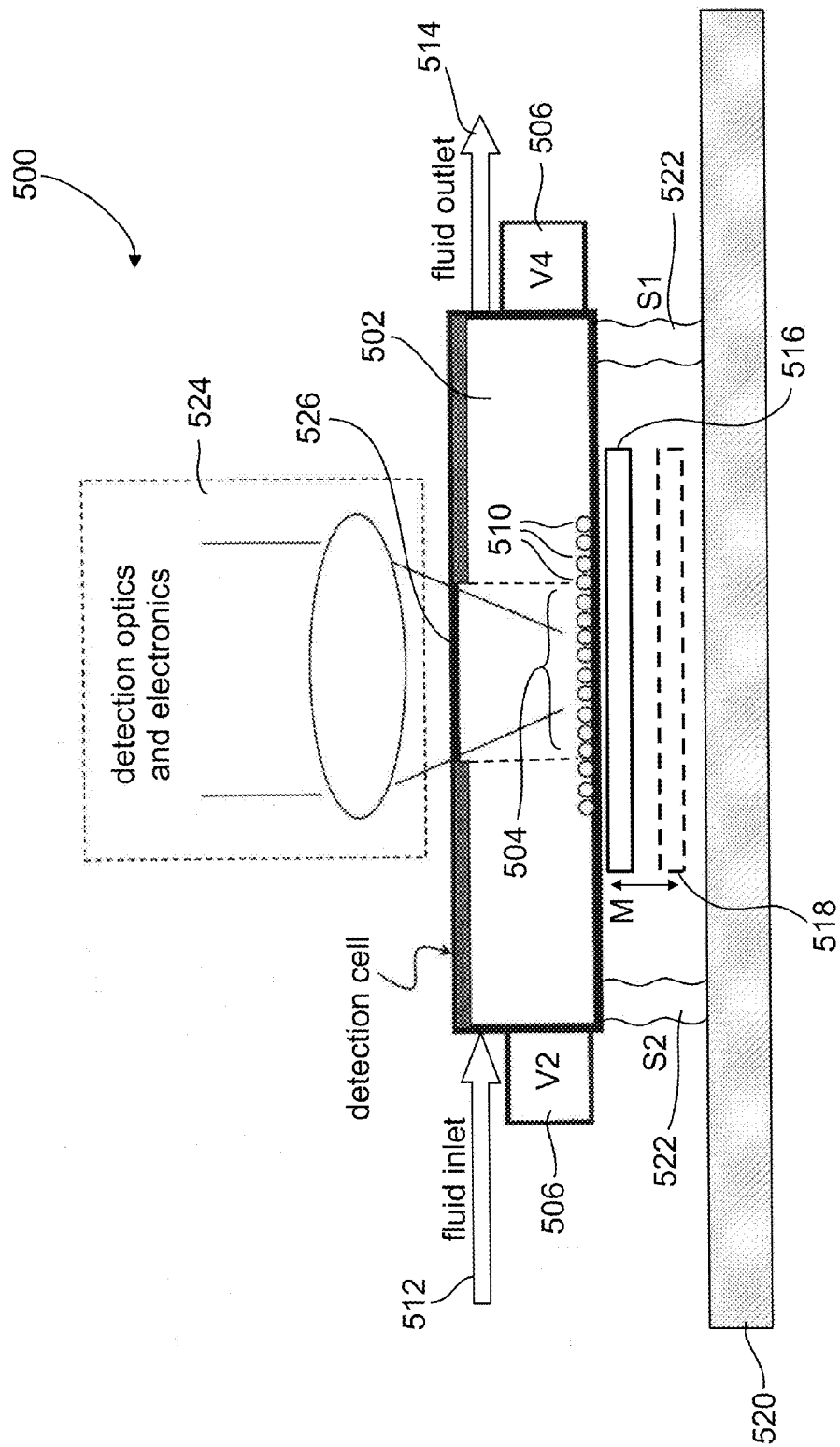
FIG. 5B is a schematic side view of the detection cell in FIG. 5A.

FIGS. 5A and 5B show a top view and a side view, respectively, of a detection station 500, in which magnets and vibrations are used to concentrate magnetic beads in a detection area, before they are measured. Although for clarity these drawings show only a single detection cell 502, optionally the detection station comprises an array of detection cells, as in detection station 122 in FIG. 1. In this case, the whole array optionally has one set of vibrators vibrating all of the detection cells together, and each detection cell optionally has its own magnet, drawing the beads towards the detection area of that detection cell.

FIG. 5A shows a detection area 504, optionally circular and in the center of detection cell 502. Vibrators 506, optionally located on each side of the detection cell, vibrate the cell, under the control of vibration controller 508. The vibrations produce momentary accelerations sufficiently great to overcome static frictional forces between the magnetic beads 510 and a bottom surface of the detection cell on which they rest. A magnet 516, not visible in the top view of FIG. 5A because it is located under the detection cell, but visible in the side view of FIG. 5B, produces a non-uniform magnetic field, which attracts the beads toward the detection area. This would be true, for example, if the magnet is a circular magnet, centered on the center of the detection area, and not too much shorter in height than its diameter, so that the gradient of the magnetic field has a radially inward pointing component over the whole bottom surface of the detection cell, or at least everywhere outside the detection area. The magnetic field gradient of such a magnet will also generally have a vertical component which pulls the magnetic beads vertically against the bottom of the detection cell, generally with a force considerably greater than the force of gravity, for the large magnetic field gradients produced by a rare earth magnet only a few millimeters in diameter. This vertical force may make the static frictional force greater than or comparable to the radial magnetic force, for a reasonably large coefficient of static friction, over much of the area of the detection cell, and if there were no vibrations, the beads might not move at all.

A fluid inlet 512 to the detection cell, and a fluid outlet 514, are shown schematically.

Optionally, magnet 516 can move vertically, close to or further away from the detection cell, for example to position 518 in FIG. 5B. Both magnet 516, and the vertical distance between magnet 516 and alternative magnet position 518, are not drawn to scale in FIG. 5B, and in fact the magnet is generally taller relative to its diameter, and moves vertically a greater distance relative to its diameter, than shown in FIG. 5B. Having the option of moving the magnet further away may make it easier to empty the detection cell after the measurement is made, to allow the cell to be used for a new set of beads, since if the magnet is too close to the bottom surface of the detection cell, it might be difficult to dislodge the beads from the surface. It may also be advantageous to be able to make adjustments in the strength of the magnetic forces on the beads, by making adjustments in the vertical position of the magnet, for example in order to optimize the concentration of beads in the detection area.

Optionally, detection cell 502 is coupled to a base 520 of the detection station by flexible springs or restraints 522. The springs or restraints optionally exert a relatively small force on the detection cell, compared to the inertial forces from the vibration, or exert no force when the detection cell is in its nominal position, but prevent the detection cell from sliding away too far from its nominal position. Alternatively, the springs exert significant force compared to the inertial forces of vibration, and the detection cell has a resonant frequency comparable to the frequency of the vibration. Optionally, the resonant system of the detection cell and springs has relatively high Q, and the vibration frequency is close to resonance, so that the amplitude of vibration is increased significantly by this high Q, potentially resulting in more effective concentration of the beads, for a given vibrator.

Detection optics 524, optionally configured as described in FIG. 3A-3D or 4A-4B, with associated detectors and other electronics, optionally view the detection area though transparent window 526 in the top of the detection cell, above the detection area.

In tests done by the inventors, good concentration of the beads in the detection area was found to occur using the following exemplary parameter values:

The detection station has an array of eight detection cells, made of a piece of aluminum, 9 cm long and 1.5 cm across, with the centers of the cells spaced 9 mm apart. The detection area in each cell is a circle 5 mm in diameter, at the center of the cell. There is a magnet placed under the center of each cell, each magnet being a cylinder 3 mm high and 4 mm in diameter, made of NdBFe. The magnetic field at the center of the detection area, 1 mm from the top surface of the magnet and along the axis of the magnet, is 2300 gauss. These magnets are sold by TMM Israel.

The vibrators are two motors taken from MACH3 Gilette razors, which have an off-axis mass on the rotor which causes them to vibrate. The two motors are mounted on opposite ends of the length of the array of cells. The speed of the motor is controlled by the voltage delivered to the motor, and different speeds were tried to find a speed which optimizes the concentration of beads. A rotation rate of 83 Hz, which produces vibrations principally at 83 Hz with some higher harmonics, and a peak-to-peak horizontal vibration amplitude of 1.5 mm, was found to produce a good concentration of beads, if allowed to continue for about 30 seconds. The entire assembly of detection cells, motors, and magnets was placed on a smooth flat base, and the horizontal motion of the assembly was limited to about 1 mm in every direction by pins protruding from the base, but the assembly was not otherwise constrained.

The magnetic beads used for these tests were the same as the beads included in the assay kits sold by Bio-Rad, for example kit 170-A4011M, the Bio-Plex Pro Human Angiogenesis 9-Plex Panel Complete Kit.

A range of values for the parameters of the detection cells, and the parameter of the use of vibrations and magnetic force to concentrate the beads, are possible. For example, the detection area is optionally about 0.5 mm, 1 mm, 2 mm, 5 mm, or 10 mm in diameter, or a larger, smaller, or intermediate length. The magnet diameter is also optionally about 0.5 mm, 1 mm, 2 mm, 5 mm, or 10 mm, or a larger, smaller, or intermediate length. The ratio of magnet diameter to magnetic height is optionally about 0.1, 0.2, 0.3, 0.5, 1, 1.5, 2, or 3, or a larger, smaller, or intermediate number. The magnet need not have a circular cross-section, or be a cylinder of uniform cross-section, although using a circular magnet with axis aligned with the center of the detection area may have the potential advantage of producing azimuthally uniform radial magnetic forces on the beads. The distance of the center of the detection area from the nearest point on the magnet is optionally about 0.2, 0.5, 1, 1.5, 2 or 3 mm, or a greater, smaller, or intermediate distance. The magnet is optionally a rare earth magnet, such as NdFeB, or SmCo, which have the potential advantage of producing strong magnetic fields and not demagnetizing easily.

The peak-to-peak vibration amplitude of the detection cells is optionally about 0.3, 0.5, 1, 2 or 3 mm, or a greater, smaller, or intermediate distance. The vibration frequency is optionally about 10, 20, 30, 50, 100, 200, or 300 Hz, or a greater, smaller, or intermediate frequency. Optionally, two or more different vibration frequencies are used, simultaneously or in succession, which may have the potential advantage of better optimizing the concentration of beads than any single vibration frequency. The vibrations are optionally applied to the detection cell for about 1 second, 3 seconds, 10 seconds, 30 seconds, 100 seconds, 5 minutes, 10 minutes, or a longer, shorter, or intermediate time. The coefficient of static friction between at least some of the beads and the surface of the detection area is optionally about 0.05, 0.1, 0.2, 0.3, 0.5, or a greater, smaller, or intermediate number. The ratio of the peak inertial force (mass times acceleration) of the beads from the vibration, and the normal component of the magnetic force pressing the beads against the detection area in the center of the detection area, is optionally about 0.05, 0.1, 0.2, 0.3, 0.5, 1, 1.5, 2, 3, 5, 10 or a greater, smaller, or intermediate number. The beads are optionally about 2, 5, 10, 20, or 50 micrometers in diameter, or a greater, smaller or intermediate distance, and the diameter of their magnetic core may be about 10%, 20%, 30%, 50%, 70% or 85% of their diameter, or a greater, smaller or number. The beads may be spherical, or another shape, and need not all be the same shape or the same size, or have the same coefficient of friction or the same magnetic core size and shape, even approximately. But using spherical beads of approximately uniform size has the potential advantage that their response to magnetic forces, and frictional forces with the detection surface, and their flow behavior, may be independent of their orientation and more predictable than if they are a non-spherical shape or of different shapes and sizes. The same remarks apply to the shape of the magnetic cores of the beads.

Vibration of the detection cell may be vertical, horizontal, or a combination of both. In general, the vibrations may be linear in any direction, circular or elliptical in any plane and with principal axes in any direction, or a combination of motions in different directions and on different planes, for example at different frequencies. As used herein, vertical refers to a direction perpendicular to the surface on which the beads are resting, but since the magnetic force attracting the beads to the surface is often greater than the force of gravity, the surface on which the beads are resting need not be horizontal with respect to gravity. Vertical and horizontal vibrations may allow the beads to overcome static friction by different mechanisms. Vertical vibrations may produce inertial forces that, at least in part of the vibration cycle, act in a direction to counter the magnetic force attracting the bead to the surface. This may reduce the static friction acting between the bead and the surface, and if great enough may even lift the bead off the surface completely, in either case allowing the bead to overcome static friction and to move horizontally under the influence of the horizontal magnetic force. Horizontal vibrations may produce inertial forces that add to the horizontal magnetic force in part of the vibration cycle, allowing the bead to overcome static friction to move in the direction of the horizontal magnetic force. In the opposite phase of the vibration cycle, the inertial force will oppose the horizontal magnetic force, either producing a weaker net horizontal force that cannot overcome static friction, or at least a weaker net horizontal force that will move the bead in the direction of the inertial force a smaller distance than when the inertial force and horizontal magnetic force are in the same direction. In either case, the bead will undergo a net drift in the direction of the horizontal magnetic force.

Optionally, for the horizontal or vertical components or both, the inertial force is not too many times greater than the magnetic force, at least for most of the beads, at least at the edge of the detection area. For example, the inertial force is no more than 3 times as great, or no more than 5 times as great, or no more than 10 times a great as the magnetic force. This has the potential advantage that beads may be drawn efficiently to concentrate in the detection area, rather than primarily being pushed back and forth with little net motion over a vibration cycle. It also has the potential advantage that the vibrator does not have to be more powerful than necessary. On the other hand, optionally the inertial force is at least 0.3 times, at least 0.5 times, or at least equal to the magnetic force, which has the potential advantage that the inertial force may be great enough to overcome static friction.

A rough estimate of the vibration frequency and amplitude sufficient to overcome static friction may be obtained by calculating a frequency and amplitude at which the inertial force on the bead is comparable to the magnetic force, whether horizontal or vertical. The magnetic force, if the bead has a spherical core made of iron or a similar high permeability magnetic material, may be approximated by the volume of the iron core, times the spatial gradient of the magnetic field energy density $B^2/\mu_0$, where B is the magnetic field strength, and $\mu_0$ is the permeability of vacuum. The inertial force may be given by half the peak-to-peak displacement, times the square of the vibration frequency $\omega$ in radians per second, times the mass of the bead. If the mass of the bead is dominated by the mass of the magnetic core, then the condition for the inertial force to be comparable to the magnetic force may depend only on the magnetic field strength, the scale length of the magnetic field gradient, which is comparable to the radius of the magnet, the vibration frequency and amplitude, and the density of the magnetic core. For a rare earth magnet with length and height both a few millimeters, and a vibration amplitude of about 1 millimeter peak to peak, for example, the frequency needed to make the inertial force comparable to the magnetic force is expected to be a few tens of Hz. This is comparable to the vibration frequencies that were found by the inventors to be most effective at causing the beads to concentrate in the center of the detection area under the influence of the magnet. So this way of estimating a vibration frequency and amplitude that will overcome static friction appears to be reasonably accurate, at least when the beads are in air, since air resistance forces on the beads may be relatively weak compared to the inertial and magnetic forces.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions, illustrate some embodiments of the invention in a non limiting fashion.

A series of IL8 assays were made, with seven different concentrations of IL8 in the sample fluid, ranging from 2 to 8000 picograms per milliliter. No vibration was used to concentrate the beads in the detection area. At each concentration, three different runs were made. For each run, the beads in the detection area were imaged with a cooled CCD detector, the Sensicam qe, sold by PCO. The integrated fluorescent emission over the detection area from the analyte complex was measured, and the number of beads in the detection area was counted, using image processing software on the digital image of the beads. On average there were about 300 beads in the detection area, in each run. The average and standard deviation of the raw integrated emission, as well as the average and standard deviation of the integrated emission normalized to the number of beads, were calculated for the three runs at each concentration of IL8. The results are shown in Table 1.

TABLE 1

| IL8 concentration, pg/ml | Raw integrated fluorescence (arbitrary units) | | Normalized integrated fluorescence (a.u.) | |
|---|---|---|---|---|
| | Mean | Percent S.D. | Mean | Percent S.D. |
| 8000 | 2340 | 43.77% | 2068 | 6.33% |
| 2000 | 1260 | 44.16% | 1280 | 12.92% |
| 5000 | 558 | 25.38% | 720 | 12.01% |
| 125 | 165 | 33.30% | 240 | 12.40% |
| 31.5 | 33 | 8.59% | 83 | 12.97% |
| 7.9 | 25 | 26.31% | 21 | 29.56% |
| 2 | 7 | 52.31% | 4 | 32.03% |

For most values of IL8 concentration, the standard deviation of the three test runs is substantially lower when the integrated fluorescence is normalized to the number of beads. This is because the number of beads, which averaged about 300, varied considerably from run to run, with a standard deviation of about 100. Only at the lowest concentrations of IL8 was the standard deviation comparable for the raw and normalized integrated fluorescence. This was due to the fact that, at the lowest concentrations of IL8, the measured amplitude of the fluorescence was close to the noise level of the detectors, so there was a high percentage standard deviation in the normalized fluorescence as well. The only exception to this was at 31.5 pg/ml, where the number of beads varied relatively little for the three runs, and was lower on average than for the other concentrations of IL8. This is presumably just due to chance, since there was no reason to think that the variation or mean of the number of beads should depend on the concentration of IL8.

Due to the large random variation in the number of beads in the detection area from run to run, accuracy of the assay is considerably improved if the number of beads is determined, and the integrated fluorescence is normalized by the number of beads. Although in this series of runs, made to illustrate this point, the integrated fluorescence is measured using a sensitive cooled CCD array, the same result would be true if a single less sensitive room temperature detector were used instead to measure the integrated fluorescence over the detection area, and a different detector were used to count or measure the number of beads.

The greater accuracy of using the normalized fluorescence, for determining the IL8 concentration, may also be seen by comparing the mean values of the raw fluorescence and the normalized fluorescence as a function of IL8 concentration. The normalized mean value is a smoother function of IL8 concentration, being approximately linear at low concentrations, and smoothly saturating at higher concentrations.

In another series of experiments, the standard deviation of the normalized fluorescence was determined, for each value of IL8 concentration, using each of the following methods:
1) Imaging the beads and directly measuring the fluorescent emission due to IL8 for each bead. The beads were not concentrated using a magnet and vibrations.
2) Measuring the integrated fluorescent emission due to IL8 from all the beads, and determining the number of beads by measuring the integrated native fluorescence of the beads, at the different wavelength than the fluorescent emission due to IL8. The native fluorescence of the beads does not depend on the IL8 concentration. The beads were not concentrated using a magnet and vibrations.

3) The same as method 2, but concentrating the beads using a magnet and vibrations.

4) For comparison, the fluorescent emission per bead was measured using an off-the-shelf Bio-Plex system, in which the beads flow one at a time past a detector, which measures the fluorescent emission of each bead. This method provides an indication of the best performance that can be expected from a bead-based fluorescence assay of IL8, but is much more expensive and slower than the first three methods.

For each of these four methods, three experiments were performed, and within each experiment, three measurements were made of the fluorescent emission, without any change in position of the beads. The standard deviation of the different measurements within each experiment was found, and a standard deviation was also found for the three experiments, using the mean value of the three measurements made within each experiment to represent that experiment. The standard deviation for the different measurements within each experiment is a measure of the degree to which random instrumental error affects the results. The standard deviation for the three experiments is a measure of the degree to which the results are affected by different conditions: for example differences in temperature, differences in the size and shape of the beads due to variations in the way they were manufactured, differences in the way the protocol for the assay was carried out, differences in the strength of the various chemical reagents due to finite shelf life or manufacturing differences, and differences in the number and distribution of beads in the detection cell.

Tables 2, 3, 4, and 5 show the percent of standard deviation for each concentration of IL8, for methods 1-4 respectively, for the different measurements within each experiment, and for the three experiments.

TABLE 2

Imaging beads

| Conc (pg/ml) | Experiment 1 | | Experiment 2 | | Experiment 3 | | 3 Experiments | |
|---|---|---|---|---|---|---|---|---|
| | Mean | Percent s.d. | Mean | Percent s.d. | Mean | Percent s.d. | Mean | Percent s.d. |
| 8000 | 5.2E+06 | 17 | 5.5E+06 | 10 | 4.1E+06 | 8 | 4.9E+06 | 16 |
| 2000 | 3.3E+06 | 9 | 3.3E+06 | 9 | 2.6E+06 | 5 | 3.1E+06 | 14 |
| 500 | 1.8E+06 | 9 | 1.6E+06 | 10 | 1.4E+06 | 2 | 1.6E+06 | 15 |
| 125 | 7.4E+05 | 16 | 4.7E+05 | 10 | 4.4E+05 | 4 | 5.5E+05 | 31 |
| 31.25 | 2.6E+05 | 12 | 1.6E+05 | 15 | 1.5E+05 | 10 | 1.9E+05 | 33 |
| 7.8 | 7.8E+04 | 11 | 6.6E+04 | 7 | 6.0E+04 | 8 | 6.8E+04 | 13 |
| 1.95 | 3.7E+04 | 4 | 3.6E+04 | 15 | 3.1E+04 | 5 | 3.5E+04 | 8 |
| Blank | 2.7E+04 | 6 | 2.4E+04 | 2 | 1.8E+04 | 20 | 2.3E+04 | 19 |

TABLE 3

Using native fluorescence to estimate number of beads, without magnet and vibration

| Conc (pg/ml) | Experiment 1 | | Experiment 2 | | Experiment 3 | | 3 Experiments | |
|---|---|---|---|---|---|---|---|---|
| | Mean | Percent s.d. | Mean | Percent s.d. | Mean | Percent s.d. | Mean | Percent s.d. |
| 8000 | 3.96 | 14 | 4.16 | 6 | 3.87 | 6 | 4.0E+00 | 4 |
| 2000 | 2.87 | 18 | 2.59 | 13 | 2.57 | 6 | 2.7E+00 | 6 |
| 500 | 1.88 | 7 | 1.47 | 12 | 1.67 | 9 | 1.7E+00 | 12 |
| 125 | 0.82 | 25 | 0.51 | 12 | 0.63 | 2 | 6.5E−01 | 24 |
| 31.25 | 0.30 | 9 | 0.19 | 10 | 0.23 | 12 | 2.4E−01 | 23 |
| 7.8 | 0.09 | 15 | 0.07 | 13 | 0.10 | 4 | 8.6E−02 | 17 |
| 1.95 | 0.05 | 3 | 0.04 | 10 | 0.05 | 19 | 4.6E−02 | 21 |
| Blank | 0.04 | 21 | 0.03 | 13 | 0.04 | 7 | 3.4E−02 | 18 |

TABLE 4

Using native fluorescence to estimate number of beads, using magnet and vibration to concentrate beads

| Conc (pg/ml) | Experiment 1 | | Experiment 2 | | Experiment 3 | | 3 Experiments | |
|---|---|---|---|---|---|---|---|---|
| | Mean | Percent s.d. | Mean | Percent s.d. | Mean | Percent s.d. | Mean | Percent s.d. |
| 8000 | 2.155 | 14 | 2.603 | 4 | 2.535 | 7 | 2.43 | 10 |
| 2000 | 1.769 | 2 | 1.941 | 3 | 1.882 | 15 | 1.86 | 5 |
| 500 | 0.826 | 13 | 0.941 | 7 | 1.069 | 4 | 0.95 | 13 |
| 125 | 0.381 | 14 | 0.397 | 4 | 0.372 | 4 | 0.38 | 3 |
| 31.25 | 0.119 | 8 | 0.117 | 8 | 0.144 | 13 | 0.13 | 12 |
| 7.8 | 0.043 | 10 | 0.051 | 18 | 0.054 | 5 | 0.05 | 11 |
| 1.95 | 0.032 | 19 | 0.023 | 8 | 0.038 | 18 | 0.03 | 24 |
| Blank | 0.026 | 20 | 0.016 | 20 | 0.024 | 12 | 0.02 | 25 |

TABLE 5

| | Using Bio-Plex system | | | | | | | |
|---|---|---|---|---|---|---|---|---|
| | Experiment 1 | | Experiment 2 | | Experiment 3 | | 3 Experiments | |
| Conc (pg/ml) | Mean | Percent s.d. | Mean | Percent s.d. | Mean | Percent s.d. | Mean | Percent s.d. |
| 8000 | 12431 | 2 | 12377 | 6 | 11425 | 5 | 12078 | 5 |
| 2000 | 9101 | 3 | 9315 | 4 | 8826 | 4 | 9080.47 | 3 |
| 500 | 4964 | 1 | 5373 | 7 | 5515 | 5 | 5284.10 | 5 |
| 125 | 2014 | 3 | 2329 | 3 | 2457 | 3 | 2266.57 | 10 |
| 31.25 | 582 | 6 | 707 | 2 | 805 | 3 | 698.10 | 16 |
| 7.8 | 150 | 1 | 194 | 2 | 251 | 3 | 198.27 | 25 |
| 1.95 | 46 | 9 | 52 | 4 | 73 | 3 | 56.90 | 25 |
| Blank | 19 | 5 | 21 | 8 | 25 | 4 | 21.60 | 14 |

Although none of methods 1-3, as shown in Tables 2-4, produced standard deviations as low as the Bio-Plex system shown in Table 5, the standard deviations for each of the methods 1-3 were reasonably small, showing that the methods using detection of integrated fluorescent emission from all beads can give reasonably good results. These methods, if they give reasonably good results, may be preferred over the Bio-Plex system, which is more complicated and takes a longer time, since individual beads are passed one at a time past a detector.

Method 2 (Table 3), which uses native fluorescence of the beads to estimate the number of beads, gives standard deviations comparable to method 1 (Table 2), which uses imaging to count the beads, demonstrating that both methods of determining the number of beads are potentially useful.

Method 3 (Table 4), using a magnet and vibrations to concentrate the beads, gives slightly lower standard deviations than method 2 (Table 3), showing that the use of a magnet and vibrations for concentrating beads is useful.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of determining a normalized quantity of an analyte adhering to beads in a detection area of a bead-based assaying system, the method comprising:
    a) causing a complex of the analyte to fluorescently or chemically emit a first light, or to release a dye;
    b) measuring an intensity of the emitted first light, integrated over the detection area, or a concentration of the dye released from the beads in the detection area, or both;
    c) causing light to interact with the beads in the detection area, the interaction not depending on whether or how much analyte is adhering to the beads;
    d) measuring a second light resulting from the interaction with the beads which does not depend on the analyte; and
    e) determining the normalized quantity of analyte by:
        i) determining a quantity of analyte adhering to the beads in the detection area, from the integrated intensity of the first light or concentration of the dye or both;
        ii) estimating a quantity of beads in the detection area from the measured second light; and
        iii) normalizing the quantity of analyte to the estimated quanity of beads;
    wherein the detection area is predefined.

2. A method according to claim 1, wherein measuring the second light comprises acquiring an image of the detection area, and estimating the quantity of beads comprises counting beads in the image using image processing software.

3. A method according to claim 1, wherein measuring the second light comprises measuring an integrated intensity of the second light from the detection area, and determining the normalized quantity of analyte comprises using the integrated intensity of the second light.

4. A method according to claim 1, wherein estimating the quantity of beads comprises estimating using only an integrated intensity of the second light from the detection area, or using only the integrated intensity of the second light from the detection area and one or more calibration parameters.

5. A method according to claim 4, wherein estimating the quantity of beads comprises estimating a quantity proportional to the integrated intensity of the second light from the detection area.

6. A method according to claim 1, wherein the interaction comprises reflection of the light from the beads.

7. A method according to claim 1, wherein the interaction comprises refraction of the light through the beads.

8. A method according to claim 1, wherein the interaction comprises exciting fluorescent emission from the beads with the light.

9. A method according to claim 8, wherein the complex is caused to emit the first light at different ranges of wavelengths than the second light.

10. A method according to claim 8, wherein the complex is caused to emit the first light fluorescently with different time dependence than the second light, by illuminating the beads with excitation light with a spectrum that varies with time.

11. A method according to claim 1, wherein the interaction comprises blocking or absorption of the light by the beads, and reflecting from or passing through areas between the beads, by the light.

12. A method according to claim 1, wherein measuring the integrated intensity of the first light, the second light, or both, comprises measuring the light after it has passed through a filter.

13. A method according to claim 1, wherein the complex is caused to emit the first light, and the beads are located in same places when measuring the first light and the second light.

14. A method according to claim 1, wherein measuring the integrated intensity of the first light is done without producing a useful image of the beads in the detection area.

15. A method according to claim 1, wherein measuring the integrated intensity of the first light is done with a non-array detector.

* * * * *